US010253300B2

(12) United States Patent
Bochkov et al.

(10) Patent No.: US 10,253,300 B2
(45) Date of Patent: Apr. 9, 2019

(54) ADAPTED RHINOVIRUS C

(71) Applicant: Wisconsin Alumni Research Foundation, Madison, WI (US)

(72) Inventors: Yury A. Bochkov, Fitchburg, WI (US); James E. Gern, Madison, WI (US); Ann C. Palmenberg, Madison, WI (US); Kelly E. Watters, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 120 days.

(21) Appl. No.: 15/232,913

(22) Filed: Aug. 10, 2016

(65) Prior Publication Data

US 2017/0044503 A1 Feb. 16, 2017

Related U.S. Application Data

(60) Provisional application No. 62/203,603, filed on Aug. 11, 2015.

(51) Int. Cl.
*C07K 14/005* (2006.01)
*C12N 7/00* (2006.01)
*A61K 39/125* (2006.01)

(52) U.S. Cl.
CPC .............. *C12N 7/00* (2013.01); *C07K 14/005* (2013.01); *C12N 2770/32721* (2013.01); *C12N 2770/32722* (2013.01)

(58) Field of Classification Search
None
See application file for complete search history.

(56) References Cited

PUBLICATIONS

Bochkov et al. (Virology, 2016, vol. 499, p. 350-360).*
Ashraf, S., Brockman-Schneider, R., Gern, J. E., 2015. Propagation of rhinovirus-C strains in human airway epithelial cells differentiated at air-liquid interface. Methods Mol.Biol. 1221, 63-70.
Bizzintino, J., Lee, W. M., Laing, I. A., Vang, F., Pappas, T., Zhang, G., Martin, A. C., Khoo, S. K., Cox, D. W., Geelhoed, G. C., McMinn, P. C., Goldblatt, J., Gern, J. E., Le Souef, P. N., 2011. Association between human rhinovirus C and severity of acute asthma in children. Eur.Respir.J. 37, 1037-1042.
Bochkov, Y. A., Palmenberg, A. C., Lee, W. M., Rathe, J. A., Amineva, S. P., Sun, X., Pasic, T. R., Jarjour, N. N., Liggett, S. B., Gern, J. E., 2011. Molecular modeling, organ culture and reverse genetics for a newly identified human rhinovirus C. Nat.Med. 17, 627-632.
Bochkov, Y. A., Watters, K., Ashraf, S., Griggs, T. F., Devries, M. K., Jackson, D. J., Palmenberg, A. C., Gern, J. E., 2015. Cadherin-related family member 3, a childhood asthma susceptibility gene product, mediates rhinovirus C binding and replication. Proc.Natl. Acad.Sci.U.S.A 112, 5485-5490.

Dorobantu, C. M., Ford-Siltz, L. A., Sittig, S. P., Lanke, K. H., Belov, G. A., van Kuppeveld, F. J., van der Schaar, H. M., 2015. GBF1- and ACBD3-independent recruitment of PI4KIIIβ to replication sites by rhinovirus 3A proteins. J.Virol. 89, 1913-1918.
Dorobantu, C. M., Albulescu, L., Lyoo, H., van Kampen, M., De Francesco, R., Lohmann, V., Harak, C., van der Schaar, H. M., Strating, J. R. P. M., Gorbalenya, A. E., van Kuppeveld, F. J. M., 2016. Mutations in Encephalomyocarditis Virus 3A Protein Uncouple the Dependency of Genome Replication on Host Factors Phosphatidylinositol 4-Kinase III+| and Oxysterol-Binding Protein. mSphere 1.
Echeverri, A. C., Dasgupta, A., 1995. Amino terminal regions of poliovirus 2C protein mediate membrane binding. Virology 208, 540-553.
Harris, J. R., Racaniello, V. R., 2003. Changes in rhinovirus protein 2C allow efficient replication in mouse cells. J.Virol. 4773-4780.
Harris, J. R., Racaniello, V. R., 2005. Amino acid changes in proteins 2B and 3A mediate rhinovirus type 39 growth in mouse cells. J.Virol. 79, 5363-5373.
Heinz, B. A., Vance, L. M., 1995. The antiviral compound enviroxime targets the 3A coding region of rhinovirus and poliovirus. J.Virol. 69, 4189-4197.
Israelsson, S., Gullberg, M., Jonsson, N., Roivainen, M., Edman, K., Lindberg, A. M., 2010. Studies of Echovirus 5 interactions with the cell surface: heparan sulfate mediates attachment to the host cell. Virus Res. 151, 170-176.
Khan, A. G., Pichler, J., Rosemann, A., Blaas, D., 2007. Human rhinovirus type 54 infection via heparan sulfate is less efficient and strictly dependent on low endosomal pH. J.Virol. 81, 4625-4632.
Klimstra, W. B., Ryman, K. D., Johnston, R. E., 1998. Adaptation of Sindbis virus to BHK cells selects for use of heparan sulfate as an attachment receptor. J.Virol. 72, 7357-7366.
Lee, W. M., Wang, W., 2003. Human rhinovirus type 16: mutant V1210A requires capsid-binding drug for assembly of pentamers to form virions during morphogenesis. J.Virol. 77, 6235-6244.
Lee, W. M., Wang, W., Rueckert, R. R., 1995. Complete sequence of the RNA genome of human rhinovirus 16, a clinically useful common cold virus belonging to the ICAM-1 receptor group. Virus Genes 9, 177-181.
McLeish, N. J., Witteveldt, J., Clasper, L., McIntyre, C., McWilliam Leitch, E. C., Hardie, A., Bennett, S., Gunson, R., Carman, W. F., Feeney, S. A., Coyle, P. V., Vipond, B., Muir, P., Benschop, K., Wolthers, K., Waris, M., Osterback, R., Johannessen, I., Templeton, K., Harvala, H., Simmonds, P., 2012. Development and assay of RNA transcripts of enterovirus species A to D, rhinovirus species a to C, and human parechovirus: assessment of assay sensitivity and specificity of real-time screening and typing methods. J.Clin. Microbiol. 50, 2910-2917.

(Continued)

*Primary Examiner* — Agnieszka Boesen
(74) *Attorney, Agent, or Firm* — Quarles & Brady LLP

(57) ABSTRACT

A mutated rhinovirus C, methods of creating and methods of propagating thereof, wherein the mutated rhinovirus shows enhanced virus yields after infection and induced visible cytopathic effect.

Figures 1A, 1B, 1C:
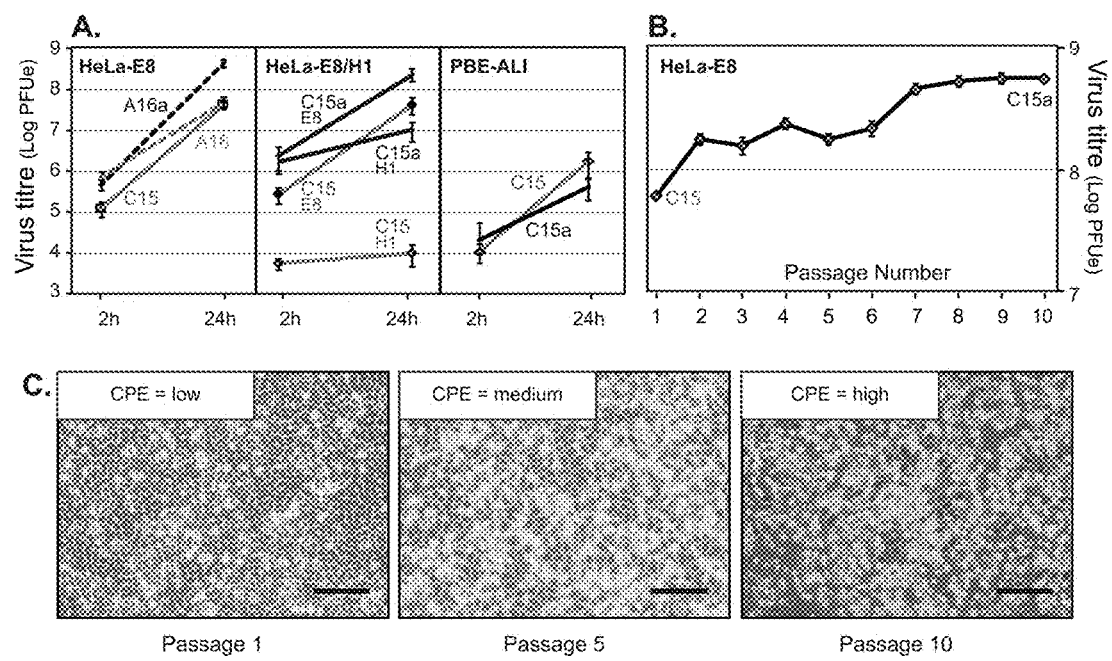

16 Claims, 12 Drawing Sheets
(8 of 12 Drawing Sheet(s) Filed in Color)
Specification includes a Sequence Listing.

(56) References Cited

PUBLICATIONS

Mousnier, A., Swieboda, D., Pinto, A., Guedan, A., Rogers, A. V., Walton, R., Johnston, S. L., Solari, R., 2014. Human rhinovirus 16 causes Golgi apparatus fragmentation without blocking protein secretion. J.Virol. 88, 11671-11685.

Nakagome, K., Bochkov, Y. A., Ashraf, S., Brockman-Schneider, R. A., Evans, M. D., Pasic, T. R., Gern, J. E., 2014. Effects of rhinovirus species on viral replication and cytokine production. J.Allergy Clin.Immunol. 134, 332-341.

Rasmussen, A. L., Racaniello, V. R., 2011. Selection of rhinovirus 1A variants adapted for growth in mouse lung epithelial cells. Virology 420, 82-88.

Reischl, A., Reithmayer, M., Winsauer, G., Moser, R., Gosler, I., Blaas, D., 2001. Viral evolution toward change in receptor usage: adaptation of a major group human rhinovirus to grow in ICAM-1-negative cells. J.Virol. 75, 9312-9319.

Sa-Carvalho, D., Rieder, E., Baxt, B., Rodarte, R., Tanuri, A., Mason, P. W., 1997. Tissue culture adaptation of foot-and-mouth disease virus selects viruses that bind to heparin and are attenuated in cattle. J.Virol. 71, 5115-5123.

Yin, F. H., Lomax, N. B., 1983. Host range mutants of human rhinovirus in which nonstructural proteins are altered. J.Virol. 48, 410-418.

\* cited by examiner

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: synthetic

<400> SEQUENCE: 1

Leu Ile Ser Ser Ala Gly
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Leu Ile Ser Ser Ala Gly Pro Ser
1               5
```

<210> SEQ ID NO 3
<211> LENGTH: 238
<212> TYPE: PRT
<213> ORGANISM: Artificial Sequence
<220> FEATURE:
<223> OTHER INFORMATION: synthetic

<400> SEQUENCE: 3

```
Val Ser Lys Gly Glu Glu Leu Phe Thr Gly Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235
```

<210> SEQ ID NO 4
<211> LENGTH: 223
<212> TYPE: PRT
<213> ORGANISM: Artificial Sequence
<220> FEATURE:
<223> OTHER INFORMATION: synthetic

<400> SEQUENCE: 4

```
Ala Ser Ser Glu Asp Val Ile Lys Glu Phe Met Arg Phe Lys Val Arg
1               5                   10                  15

Met Glu Gly Ser Val Asn Gly His Glu Phe Glu Ile Glu Gly Glu Gly
            20                  25                  30

Glu Gly Arg Pro Tyr Glu Gly Thr Gln Thr Ala Lys Leu Lys Val Thr
        35                  40                  45

Lys Gly Gly Pro Leu Pro Phe Ala Trp Asp Ile Leu Ser Pro Gln Phe
    50                  55                  60

Gln Tyr Gly Ser Lys Val Tyr Val Lys His Pro Ala Asp Ile Pro Asp
65                  70                  75                  80
```

```
Tyr Lys Lys Leu Ser Phe Pro Glu Gly Phe Lys Trp Glu Arg Val Met
                 85                  90                  95

Asn Phe Glu Asp Gly Gly Val Val Thr Val Thr Gln Asp Ser Ser Leu
            100                 105                 110

Gln Asp Gly Ser Phe Ile Tyr Lys Val Lys Phe Ile Gly Val Asn Phe
        115                 120                 125

Pro Ser Asp Gly Pro Val Met Gln Lys Lys Thr Met Gly Trp Glu Ala
    130                 135                 140

Ser Thr Glu Arg Leu Tyr Pro Arg Asp Gly Val Leu Lys Gly Glu Ile
145                 150                 155                 160

His Lys Ala Leu Lys Leu Lys Asp Gly Gly His Tyr Leu Val Glu Phe
                165                 170                 175

Lys Ser Ile Tyr Met Ala Lys Lys Pro Val Gln Leu Pro Gly Tyr Tyr
            180                 185                 190

Tyr Val Asp Ser Lys Leu Asp Ile Thr Ser His Asn Glu Asp Tyr Thr
        195                 200                 205

Ile Val Glu Gln Tyr Glu Arg Ala Glu Gly Arg His His Leu Phe
    210                 215                 220
```

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ttaaaactgg gtataggttg ttcc                                      24

<210> SEQ ID NO 6
<211> LENGTH: 22
<212> TYPE: DNA
<213> ORGANISM: Artificial Sequence
<220> FEATURE:
<223> OTHER INFORMATION: synthetic

<400> SEQUENCE: 6
tggatgggtc ctgagaaaag tc                                        22

<210> SEQ ID NO 7
<211> LENGTH: 23
<212> TYPE: DNA
<213> ORGANISM: Artificial Sequence
<220> FEATURE:
<223> OTHER INFORMATION: synthetic

<400> SEQUENCE: 7
actttgccct gggtgtgtat gat                                       23

<210> SEQ ID NO 8
<211> LENGTH: 23
<212> TYPE: DNA
<213> ORGANISM: Artificial Sequence
<220> FEATURE:
<223> OTHER INFORMATION: synthetic

<400> SEQUENCE: 8
actttgccct gggtgtgtat gat                                       23

<210> SEQ ID NO 9
<211> LENGTH: 22
<212> TYPE: DNA

```
<213> ORGANISM: Artificial Sequence
<220> FEATURE:
<223> OTHER INFORMATION: synthetic

<400> SEQUENCE: 9
tcatttctag gggcagaaca ag                                              22

<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
tggtgcactc atagtcgcgg t                                               21

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
aacgccaagg cttgccaacg                                                 20

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
ctattgtgga ttctggggtt gcgt                                            24

<210> SEQ ID NO 13
<211> LENGTH: 29
<212> TYPE: DNA
<213> ORGANISM: Artificial Sequence
<220> FEATURE:
<223> OTHER INFORMATION: synthetic

<400> SEQUENCE: 13
gactcccggg gcctggaaca ttggtacta                                       29

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14
atattgggtg ccatggagat tggt                                            24

<210> SEQ ID NO 15
<211> LENGTH: 31
<212> TYPE: DNA
<213> ORGANISM: Artificial Sequence
<220> FEATURE:
<223> OTHER INFORMATION: synthetic

<400> SEQUENCE: 15
gattgtcgac ctaactctag tggacctgat g                                    31
```

<210> SEQ ID NO 16
<211> LENGTH: 21
<212> TYPE: DNA
<213> ORGANISM: Artificial Sequence
<220> FEATURE:
<223> OTHER INFORMATION: synthetic

<400> SEQUENCE: 16
tgggtgagtc ctctagcgat t                                    21

<210> SEQ ID NO 17
<211> LENGTH: 31
<212> TYPE: DNA
<213> ORGANISM: Artificial Sequence
<220> FEATURE:
<223> OTHER INFORMATION: synthetic

<400> SEQUENCE: 17
gttatctaga ccataggcat gaaccagttt g                         31

<210> SEQ ID NO 18
<211> LENGTH: 23
<212> TYPE: DNA
<213> ORGANISM: Artificial Sequence
<220> FEATURE:
<223> OTHER INFORMATION: synthetic

<400> SEQUENCE: 18
cgttggtgtt ctgggatgaa cct                                  23

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ccgtcaattg tgacagagtc acca                                 24

<210> SEQ ID NO 20
<211> LENGTH: 25
<212> TYPE: DNA
<213> ORGANISM: Artificial Sequence
<220> FEATURE:
<223> OTHER INFORMATION: synthetic

<400> SEQUENCE: 20
agtagagcag ctgaggcatg agaat                                25

<210> SEQ ID NO 21
<211> LENGTH: 27
<212> TYPE: DNA
<213> ORGANISM: Artificial Sequence
<220> FEATURE:
<223> OTHER INFORMATION: synthetic

<400> SEQUENCE: 21
gaattctaga taactgtgcg gtggtgc                              27

<210> SEQ ID NO 22
<211> LENGTH: 25
<212> TYPE: DNA
<213> ORGANISM: Artificial Sequence
<220> FEATURE:

<223> OTHER INFORMATION: synthetic

<400> SEQUENCE: 22
gaagtttggt tacatccttt gtcac                                              25

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
tgtactgccc ttgtctggtg gag                                                23

<210> SEQ ID NO 24
<211> LENGTH: 26
<212> TYPE: DNA
<213> ORGANISM: Artificial Sequence
<220> FEATURE:
<223> OTHER INFORMATION: synthetic

<400> SEQUENCE: 24
attatagcat atggtgatga tgtagt                                             26

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
atatcccggg ttcgaatcga                                                    20

<210> SEQ ID NO 26
<211> LENGTH: 21
<212> TYPE: DNA
<213> ORGANISM: Artificial Sequence
<220> FEATURE:
<223> OTHER INFORMATION: synthetic

<400> SEQUENCE: 26
atatcccggg ttcgaatcga t                                                  21

<210> SEQ ID NO 27
<211> LENGTH: 33
<212> TYPE: DNA
<213> ORGANISM: Artificial Sequence
<220> FEATURE:
<223> OTHER INFORMATION: synthetic

<400> SEQUENCE: 27
gtaaccaaca acaaagggtt gatgcaaata atg                                     33

<210> SEQ ID NO 28
<211> LENGTH: 33
<212> TYPE: DNA
<213> ORGANISM: Artificial Sequence
<220> FEATURE:
<223> OTHER INFORMATION: synthetic

<400> SEQUENCE: 28
cattatttgc atcaacccctt tgttgttggt tac                                    33

```
<210> SEQ ID NO 29
<211> LENGTH: 33
<212> TYPE: DNA
<213> ORGANISM: Artificial Sequence
<220> FEATURE:
<223> OTHER INFORMATION: synthetic

<400> SEQUENCE: 29
actcaaccat aaagagggat tttaattatg tgc                          33

<210> SEQ ID NO 30
<211> LENGTH: 30
<212> TYPE: DNA
<213> ORGANISM: Artificial Sequence
<220> FEATURE:
<223> OTHER INFORMATION: synthetic

<400> SEQUENCE: 30
aatccctctt tatggttgag tttgctttac                              30

<210> SEQ ID NO 31
<211> LENGTH: 25
<212> TYPE: DNA
<213> ORGANISM: Artificial Sequence
<220> FEATURE:
<223> OTHER INFORMATION: synthetic

<400> SEQUENCE: 31
acatcagcta gcatacattg gcgct                                   25

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32 ttcacccct ccaggaggtg gat                                      23

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33
actctgatac tgcctgacca gttg                                    24

<210> SEQ ID NO 34
<211> LENGTH: 37
<212> TYPE: DNA
<213> ORGANISM: Artificial Sequence
<220> FEATURE:
<223> OTHER INFORMATION: syntehtic

<400> SEQUENCE: 34
gtaactaata acaaaggttt aatgcaaatc atgtatg                      37

<210> SEQ ID NO 35
<211> LENGTH: 38
<212> TYPE: DNA
<213> ORGANISM: Artificial Sequence
<220> FEATURE:
<223> OTHER INFORMATION: synthetic
```

```
<400> SEQUENCE: 35
gcattaaacc tttgttatta gttactatag ttacttcc                              38

<210> SEQ ID NO 36
<211> LENGTH: 30
<212> TYPE: DNA
<213> ORGANISM: Artificial Sequence
<220> FEATURE:
<223> OTHER INFORMATION: synthetic

<400> SEQUENCE: 36
acataatatg ctgagcctaa accagtaaag                                       30

<210> SEQ ID NO 37
<211> LENGTH: 56
<212> TYPE: DNA
<213> ORGANISM: Artificial Sequence
<220> FEATURE:
<223> OTHER INFORMATION: synthetic

<400> SEQUENCE: 37
cttatcctga ggagctccac caccttaaag agacacatag acagagtaca gcaggc          56

<210> SEQ ID NO 38
<211> LENGTH: 22
<212> TYPE: DNA
<213> ORGANISM: Artificial Sequence
<220> FEATURE:
<223> OTHER INFORMATION: synthetic

<400> SEQUENCE: 38
gcagatgtag ggacagcaac ac                                               22

<210> SEQ ID NO 39
<211> LENGTH: 25
<212> TYPE: DNA
<213> ORGANISM: Artificial Sequence
<220> FEATURE:
<223> OTHER INFORMATION: synthetic

<400> SEQUENCE: 39
atttccaagt acaccaccac actga                                            25

<210> SEQ ID NO 40
<211> LENGTH: 29
<212> TYPE: DNA
<213> ORGANISM: Artificial Sequence
<220> FEATURE:
<223> OTHER INFORMATION: synthetic

<400> SEQUENCE: 40
aagtaacgta cggtaaatca ataccatac                                        29

<210> SEQ ID NO 41
<211> LENGTH: 588
<212> TYPE: DNA
<213> ORGANISM: Artificial Sequence
<220> FEATURE:
<223> OTHER INFORMATION: synthetic

<400> SEQUENCE: 41
tggtaccaaa ctgatttcat cccttcagtt aacgcaggca caggtaccat cattgctact      60
tgtagcgcct gccctgacat gtctgttagg atgatgaggg atagtccaat gatgaagcaa     120
gaagggaagc tccaaaacaa tgatcccgtg gaatccttca ttcacacaac gctagaggaa     180
```

```
gtactagttg tgccagacac caaaccatca ggcccacaac atactaccaa accatcagca    240
cttggggcga tggaaattgg agcatcaagc gatgcaactc ctgaatcagt gatagaaact    300
aggtatgtgt tcaacacaaa caccaatgca gaagctgaca ttgaaatgtt tctgggtaga    360
tcagctttat gggctaattt gacacttaga gaaggattca ctgaatggga gataaatttc    420
caggagaatg cacacatcag gaagaagttt gaactattca cctatattag gtttgacatg    480
gaagttacaa tagtaacgaa caacaaaggg ttaatgcaga tcatgttcgt gccacctgga    540
atcactggtc caaagaatgc tgaggatatt cgatgggatt ccgcctca               588
```

<210> SEQ ID NO 42
<211> LENGTH: 25
<212> TYPE: DNA
<213> ORGANISM: Artificial Sequence
<220> FEATURE:
<223> OTHER INFORMATION: synthetic

<400> SEQUENCE: 42

```
atccttgcta gcacaaattt ggaca                                         25
```

<210> SEQ ID NO 43
<211> LENGTH: 40
<212> TYPE: DNA
<213> ORGANISM: Artificial Sequence
<220> FEATURE:
<223> OTHER INFORMATION: synthetic

<400> SEQUENCE: 43

```
tggttctaca gtaaaaaggg atttcaacta tgttcattac                         40
```

<210> SEQ ID NO 44
<211> LENGTH: 35
<212> TYPE: DNA
<213> ORGANISM: Artificial Sequence
<220> FEATURE:
<223> OTHER INFORMATION: synthetic

<400> SEQUENCE: 44

```
tgaaatccct ttttactgta gaaccagccc ttcca                              35
```

<210> SEQ ID NO 45
<211> LENGTH: 25
<212> TYPE: DNA
<213> ORGANISM: Artificial Sequence
<220> FEATURE:
<223> OTHER INFORMATION: synthetic

<400> SEQUENCE: 45

```
atgttctggg ccctgtagag tagct                                         25
```

<210> SEQ ID NO 46
<211> LENGTH: 22
<212> TYPE: DNA
<213> ORGANISM: Artificial Sequence
<220> FEATURE:
<223> OTHER INFORMATION: synthetic

<400> SEQUENCE: 46

```
agaagcaatg cttggtgtgc at                                            22
```

<210> SEQ ID NO 47
<211> LENGTH: 24
<212> TYPE: DNA

```
<213> ORGANISM: Artificial Sequence
<220> FEATURE:
<223> OTHER INFORMATION: synthetic

<400> SEQUENCE: 47
tctacaatcc acagtgtcat tggt                                           24

<210> SEQ ID NO 48
<211> LENGTH: 22
<212> TYPE: DNA
<213> ORGANISM: Artificial Sequence
<220> FEATURE:
<223> OTHER INFORMATION: synthetic

<400> SEQUENCE: 48
acaatacgcg agcacaaagt tc                                             22

<210> SEQ ID NO 49
<211> LENGTH: 28
<212> TYPE: DNA
<213> ORGANISM: Artificial Sequence
<220> FEATURE:
<223> OTHER INFORMATION: synthetic

<400> SEQUENCE: 49
gataatcaga gtgtagtaat aatggatg                                       28

<210> SEQ ID NO 50
<211> LENGTH: 27
<212> TYPE: DNA
<213> ORGANISM: Artificial Sequence
<220> FEATURE:
<223> OTHER INFORMATION: synthetic

<400> SEQUENCE: 50
agtcatcttc tgattcaggt atgtact                                        27

<210> SEQ ID NO 51
<211> LENGTH: 22
<212> TYPE: DNA
<213> ORGANISM: Artificial Sequence
<220> FEATURE:
<223> OTHER INFORMATION: synthetic

<400> SEQUENCE: 51
ttagaaattc ttcagatccg ca                                             22
```

ADAPTED RHINOVIRUS C

CROSS-REFERENCE TO RELATED APPLICATIONS

This application claims the benefit of U.S. Provisional Patent Application Ser. No. 62/203,603 filed on Aug. 11, 2015. This application is incorporated by reference in its entirety.

STATEMENT REGARDING FEDERALLY SPONSORED RESEARCH OR DEVELOPMENT

This invention was made with government support under AI104317 awarded by the National Institutes of Health. The government has certain rights in the invention.

BACKGROUND

Rhinovirus C species (RV-C) was discovered in 2006 and is of special interest because RV-C isolates can cause more severe illnesses in children compared to other rhinoviruses and are closely associated with asthma exacerbations. Applicants developed the first culture systems for RV-C (sinus mucosal organ culture and air-liquid interface (ALI) culture of differentiated airway epithelial cells), the first virus production methods (reverse genetics from viral RNA synthesized in vitro) and discovered that human cadherin-related family member 3 (CDHR3) protein mediates virus binding and replication.

Human rhinoviruses (RVs) are classified into three species (A, B and C) of the Picornaviridae family. They are subdivided further into more than 160 types that are responsible for the majority of upper respiratory tract infections (common colds), and also many lower respiratory tract illnesses (Hayden, 2004; Gem, 2010). The first isolates in the RV-C species were described in 2006 (Lamson et al., 2006; Arden et al., 2006). Consequently, they were classified into 55 types, believed to be synonymous with serotypes, according to sequence diversity thresholds observed in the capsid-coding proteins, VP1 and VP4 (Simmonds et al., 2010; McIntyre et al., 2013). The RV-A and RV-C tend to cause more severe illnesses in young children compared to RV-B. However, RV-C infections are those more closely linked with childhood asthma exacerbations (Bizzintino et al., 2011; Calvo et al., 2010; Cox et al., 2013; Drysdale et al., 2014; Fawkner-Corbett et al., 2015; Lee et al., 2012).

Prototype RV-A and RV-B laboratory strains, representing major and minor receptor groups, are commonly used in vitro to study virus biology and host cell response. These include RV-A1 (subtypes a and b), RV-A2, RV-A16 and RV-B14 (Stanway et al., 1984; Skern et al., 1985; Hughes et al., 1988; Kim et al., 1989; Lee et al., 1995). These particular strains have been passaged multiple times in continuous cell lines (such as HeLa) after their initial clinical isolations, and all of them are now available as fully-sequenced cDNA reagents. As a result, the adapted forms of these recombinant viruses replicate well and induce strong cytopathic effect (CPE) in cell culture (Conant & Hamparian, 1968). In contrast, typical unpassaged clinical RV isolates generally replicate less efficiently and without visible CPE in the same cell lines, even though their replication in natural host cells (differentiated airway epithelial cells) remains quite robust (Nakagome et al., 2014).

It has been described that human cadherin-related family member 3 (CDHR3) protein can mediate RV-C binding and replication when it is expressed in cultured cells. A transduced HeLa cell line derivative (HeLa-E8) which stably expresses the CDHR3-$Y_{529}$ variant supports propagation of RV-C isolates in these cultures after infection (Bochkov et al., 2015). The HeLa-E8 cell line propagation method is the subject of pending U.S. patent application Ser. No. 14/836,327, incorporated herein in its entirety. C15, a recombinant derivative of a clinical RV-C isolate (Bochkov et al., 2011) replicates to detectable titers in HeLa-E8, yet the progeny yields of this virus after infection never reach the levels achieved in parallel infections by RV-A or RV-B adapted laboratory strains. Moreover, C15 infections of HeLa-E8 cells do not induce visible CPE, a useful phenotypic marker of effective, productive viral synthesis.

SUMMARY OF THE INVENTION

In one embodiment, the present invention is an isolated mutated rhinovirus C, wherein the mutation comprises at least one mutation selected from the group consisting of $T_{125}K$ in rhinovirus C protein VP1, a mutation structurally analogous to $T_{125}K$ in non-C15 strains, $E_{41}K$ in rhinovirus C protein 3A, and a mutation that is a positional equivalent of $E_{41}K$ in non-C15 strains. Preferably, the rhinovirus C is a clinical isolate selected from the group consisting of C15, C41, and C2. In one embodiment, the rhinovirus C is clinical isolate C15 and the mutation comprises both $T_{125}K$ in rhinovirus C protein VP1 and $E_{41}K$ in rhinovirus C protein 3A. In another embodiment, the rhinovirus C is clinical isolate C15 and the mutation comprises $T_{125}K$ in rhinovirus C protein VP1. In another embodiment, the rhinovirus C is clinical isolate C15 and the mutation comprises $E_{41}K$ in rhinovirus C protein 3A.

In one embodiment, the rhinovirus C is clinical isolate C41 and the mutation comprises a mutation which is the positional equivalent of $E_{41}K$ in rhinovirus C protein 3A in strain C15. In another embodiment, the rhinovirus C is clinical isolate C2 and the mutation comprises a mutation which is the positional equivalent of $E_{41}K$ in rhinovirus C protein 3A in strain C15.

In one embodiment the mutated rhinovirus C additionally comprises a reporter. Preferably, the reporter is selected from the group consisting of DsRed and GFP. In one embodiment, the reporter is positioned upstream of a viral open reading frame and linked by SEQ ID NO:1. In another embodiment, the reporter is between VP1 and 2A and linked by SEQ ID NO:2.

In one embodiment, the present invention is an infected transduced cell line, wherein the cell line expresses CDHR3 and is infected with the mutated rhinovirus C as previously described.

In one embodiment, the present invention is a method of propagating rhinovirus C, comprising the step of infecting a transduced cell line expressing CDHR3 with the mutated rhinovirus C of as previously described. Preferably, the cell line is a HeLa-E8 cell line.

In one embodiment, the present invention is a method of creating a mutated rhinovirus C, wherein the method comprises the steps of introducing at least one mutation selected from the group consisting of $T_{125}K$ in rhinovirus C protein VP1, a mutation structurally analogous to $T_{125}K$ in non-C15 strains, $E_{41}K$ in rhinovirus C protein 3A, and a mutation that is a positional equivalent of $E_{41}K$ in non-C15 strains, and isolating the mutated rhinovirus C.

BRIEF DESCRIPTION OF THE DRAWINGS

This patent application file contains at least one drawing executed in color. Copies of this patent or patent application publication with color drawings will be provided by the Office upon request and payment of the necessary fee.

FIGS. 1A-1C—C15 adaptation. (A) Monolayers of HeLa-E8 and HeLa-H1, or differentiated cultures of PBE-ALI cells from three donors, grown in 12-well plates were infected with A16a, C15 or C15a virus at $2\times10^6$ PFUe per well. After 2 h (binding) or 24 h (replication) incubation at 34° C., the cells were analyzed for viral RNA signals by RT-qPCR (means±s.d., n≥3). (B) C15 virus was passaged serially in HeLa-E8 cells as described in Results. Each passage (72 h p.i., MOI=10) was evaluated for virus titer (PFUe) by RT-qPCR. Polyclonal C15a is defined as the Passage 10 material. (C) Passage 1, Passage 5 and Passage 10 infected cells were visualized (72 h p.i.) and photographed by light microscopy. Scale bar is 100 μm. Relative CPE is indicated.

Figures 2A, 2B, 2C:
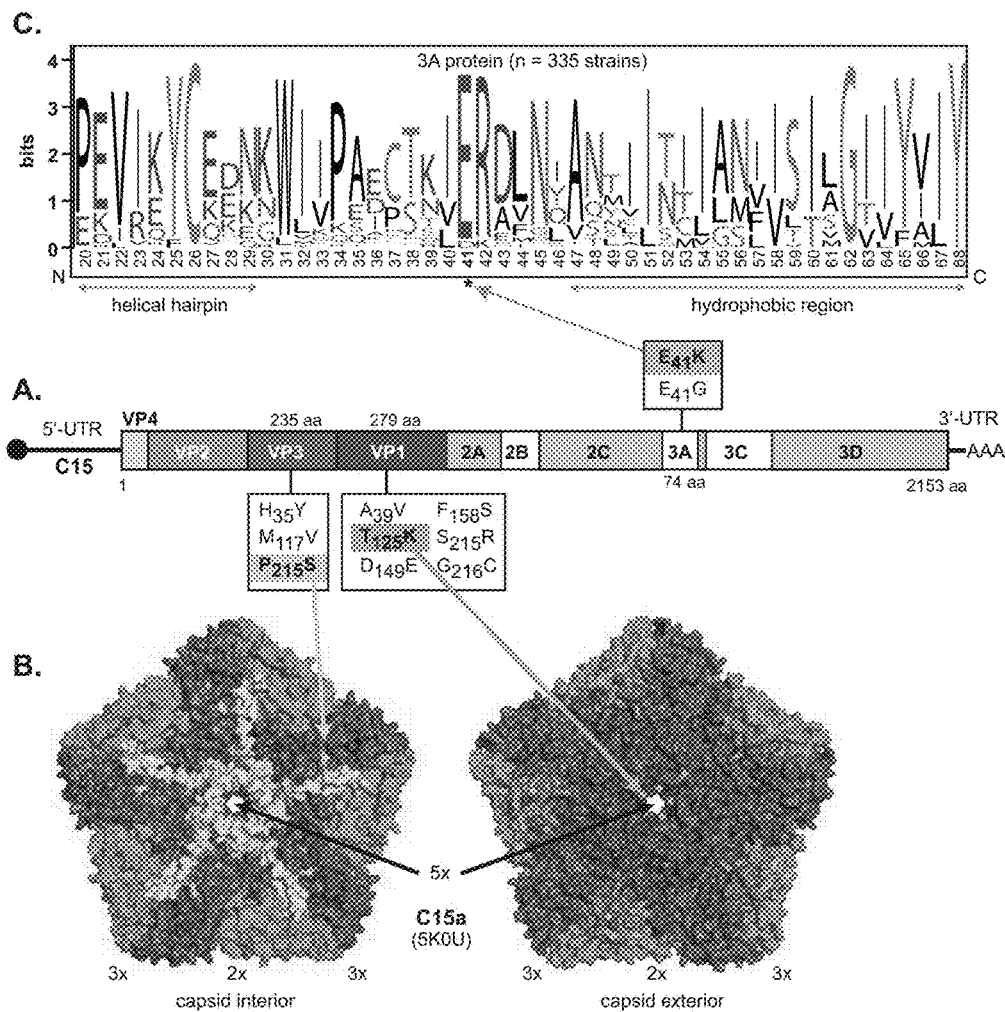

FIGS. 2A-2C—C15a mutations. (A) Schematic of the C15 genome shows all missense mutations identified in coding (VP1 and VP3) and non-coding (3A) regions of the C15a population. The dominant mutations (found in >5 out of 10 clones) are highlighted. (B) Depiction of a C15a capsid pentamer structure (PDB 5KOU) localizes VP3 $P_{215}$ and VP1 $T_{125}$ to the interior and exterior surfaces, respectively. (C) WebLogo (Crooks et al., 2004) depiction for an amino acid sequence alignment of RV sequences (n=335) shows $E_{41}$ as the dominant residue in this highly conserved position of the 3A protein. Color coding in this panel is by residue type, the overall height of the stack indicates the sequence conservation, while the height of symbols within the stack indicates the relative frequency of each amino acid at that position.

Figures 3A, 3B:
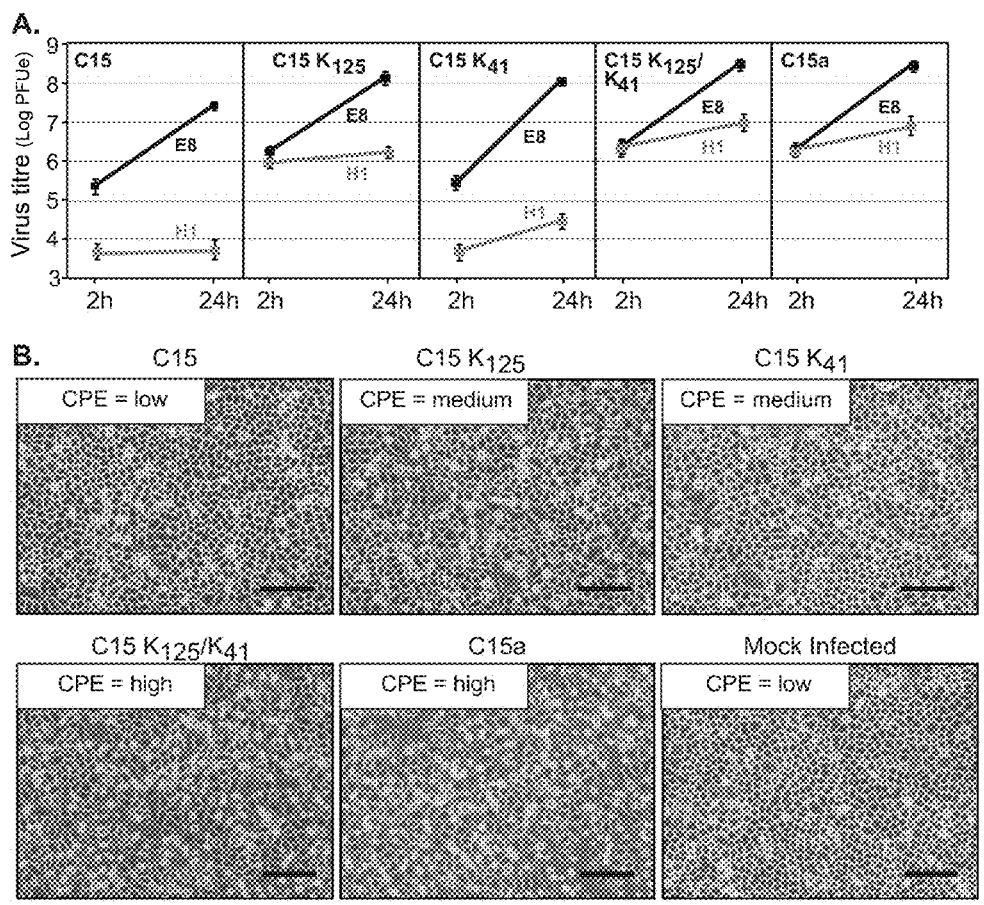

FIGS. 3A-3B—C15a recombinants. (A) Recombinant C15 and recombinant C15 harboring one or both dominant adaptive mutations (VP1 $T_{125}K$, 3A $T_{41}K$) and polyclonal C15a were tested for relative binding affinities (2 h) and replication potential (24 h) in HeLa-E8 and HeLa-H1 cells. Infections per well were initiated with equival$_{ent}$ $2\times10^6$ PFUe. Virus titers were measured by RT-qPCR (means±s.d., n≥3). (B) Infected cells were visualized and photographed by light microscopy at 72 h p.i. Scale bar is 100 μm. Relative CPE is indicated.

FIGS. 4A-4E—Heparin and heparan sulfate effects. (A) Virus samples ($5\times10^5$ PFUe) were incubated with heparin (2 mg/ml) or medium alone (no heparin) for 30 min at 34° C., before inoculation of HeLa-E8 cells. After an attachment period (30 min at room temp, 30 min at 34° C.) the cells were washed (3×PBS), harvested and tested by RT-qPCR for the attached virus RNA signals (means±s.d., n≥3). (*) indicates p<0.05 significance (t-test). (B) C15a and C15 $K_{125}$ ($5\times10^5$ PFUe) were incubated with heparin or heparan sulfate (1 mg/ml) as in A, before HeLa-E8 infections and virus binding assays. (C) The C15a experiment in A was repeated using different doses of heparin in the preincubation. (D) HeLa-E8 cells (12 well-plates) were treated (37° C., 2 h) with the indicated dose (U) of heparinase I before inoculation with C15a virus ($5\times10^5$ PFUe) and tested for virus binding as in A. $_{(E)}$ C15a and recombinant C15 $K_{125}/K_{41}$ viruses ($5\times10^5$ PFUe) were incubated with heparin (1 mg/ml, 30 min, 34° C.) before inoculation of HeLa-E8 or HeLa-H1 cells. After an attachment period (30 min at room temp, 30 min at 34° C.), the cells were washed with PBS (3×). Cells were harvested and assayed for the attached virus (1 h p.i.) and progeny virus (24 h p.i.) RNA signals by RT-qPCR (means±s.d., n=3).

Figure 5:
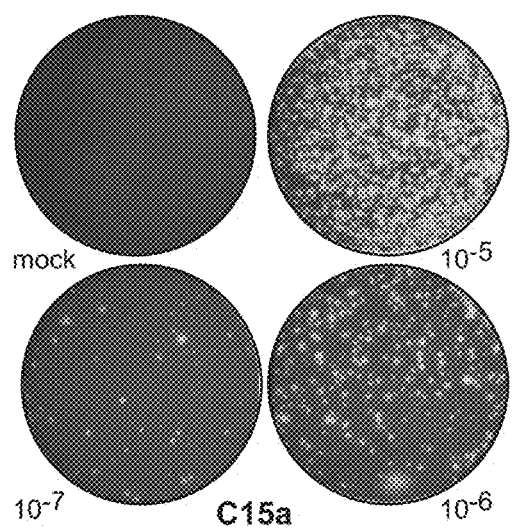

FIG. 5—C15a plaque assay. Semi-confluent monolayers of HeLa-E8 cells were inoculated with serial dilutions of C15a. After an attachment period (30 min), the plates were overlaid with agarose (Seakem ME, 0.8% in P6 medium) and incubated at 34° C. for 96 h before the cells were fixed and stained with crystal violet.

Figures 6A, 6B:
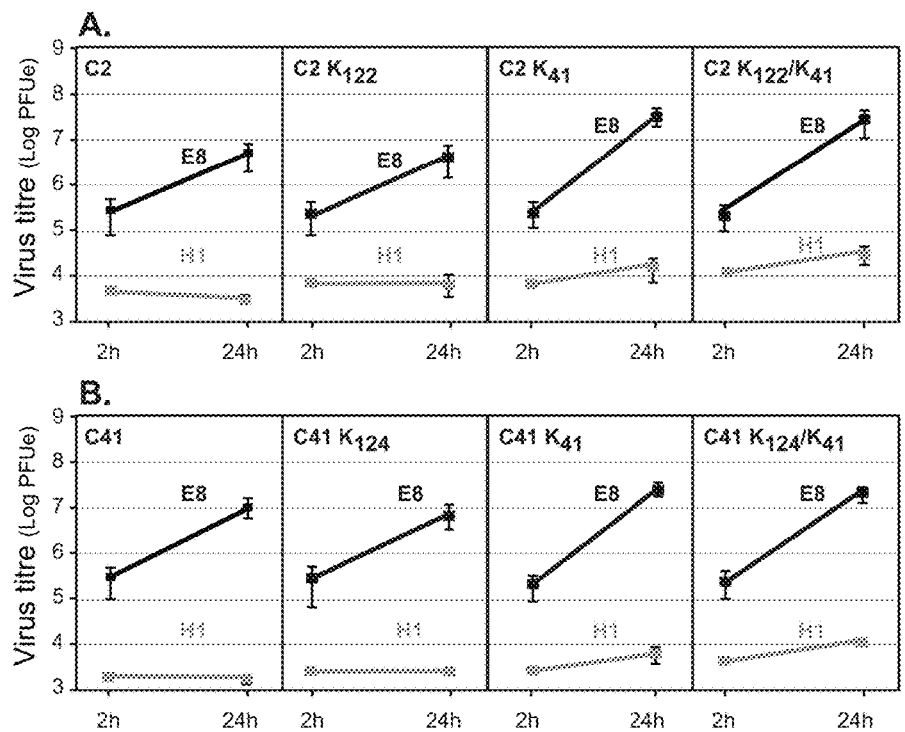

FIGS. 6A-6B—C2 and C41 recombinants. Recombinant (A) C2 and (B) C41 viruses engineered to express the indicated VP1 mutations ($K_{122}$ or $K_{124}$ respectively) and/or 3A $K_{41}$ mutation, were infected into HeLa-E8 or HeLa-H1 cells (12-well plates, $2\times10^6$ PFUe per well). Virus titer was measured by RT-qPCR (means±s.d., n≥3) as in FIG. 1A.

Figures 7A, 7B, 7C:
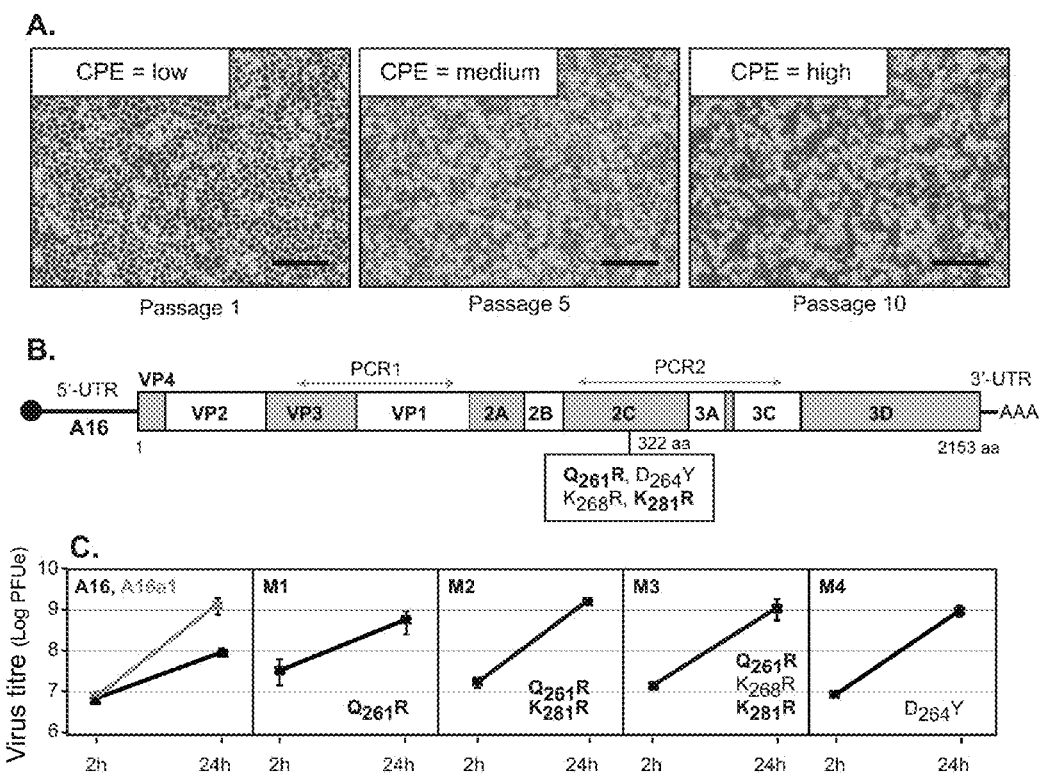

FIGS. 7A-7C—A16 adaptation. A recombinant A16 virus (pR16.939), derived from a clinical isolate, was passaged serially in HeLa-H1 similar to FIG. 1C. (A) At the indicated passages (72 h p.i.), cells were visualized by light microscopy. Scale bar, 100 μm. Relative CPE is indicated. (B) Two regional PCR-derived cDNA amplicons (PCR1 and PCR2) from the A16 passage 10 population were sequenced to identify adaptation-specific mutations. Those identified in the 2C gene are indicated; high frequency mutations (found in >5 out of 10 clones) are boldface. (C) Engineered recombinant viruses with the indicated mutation(s) were tested relative to A16 and A16a1 (adapted population) samples, for cell-binding (2 h) and replication (24 h) in HeLa-H1 cells (12-well plates, $10^6$ PFUe per well). Virus titers were determined by RT-qPCR (means±s.d., n=3).

Figures 8A, 8B, 8C:
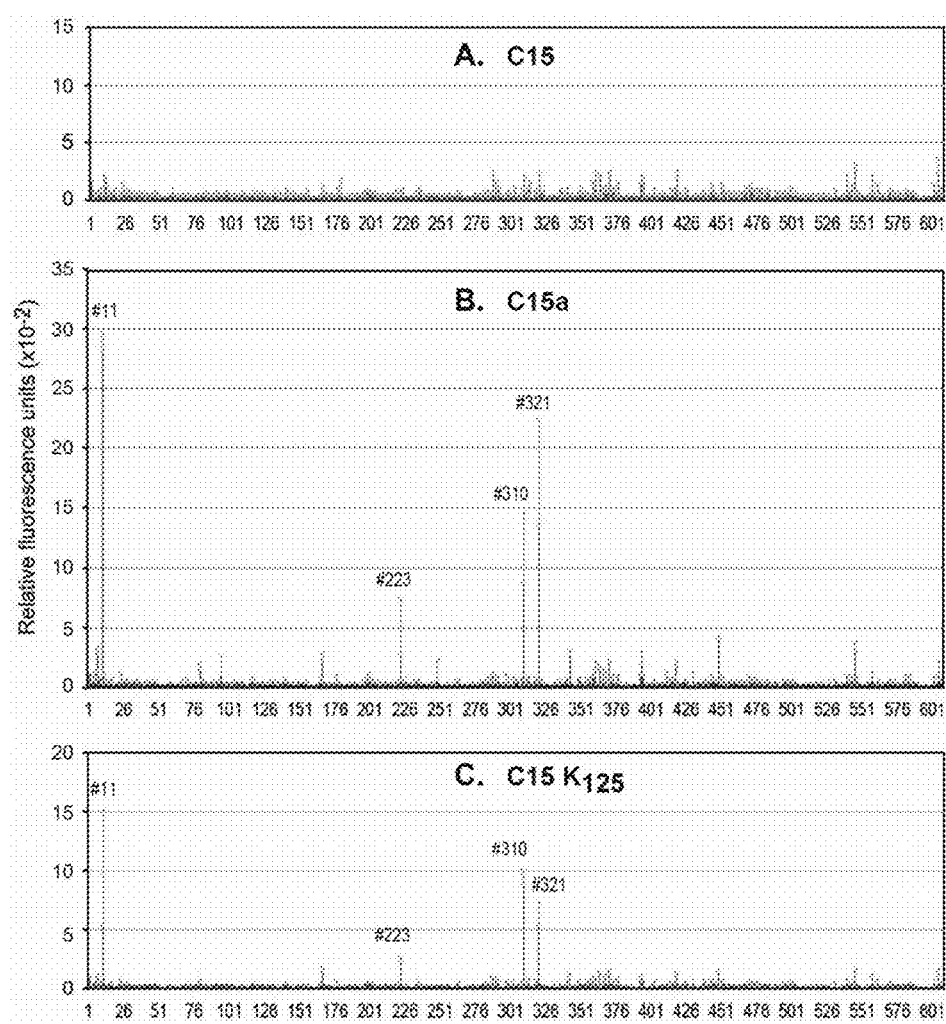

FIGS. 8A-8C—C15 reactivity to a glycan array. (A) Recombinant C15, (B) polyclonal C15a, and (C) recombinant C15 $K_{125}$ viruses were screened for binding to a mammalian glycan array containing 609 targets (Consortium for Functional Glycomics). The C15 preparation showed no positive signal. The other viruses had only low levels of reactivity to a small fraction of the tested panel of sialylated glycans and disaccharides, including #11 (Neu5Acb-5p8), #223 (Fuca 1-2(6S)Galb1-4(6S)Glcb-Sp0), #310 (GlcNAcb1-3Man-Sp10), and #321 (Neu5Aca2-8Neu5Acb-5p17). Of these, #11 and #310 are considered probable spurious background reactions by the test Consortium, and neither #223 or #321 register as strong enough signals to be considered reliable evidence for any specific interaction.

Figures 9A, 9B:
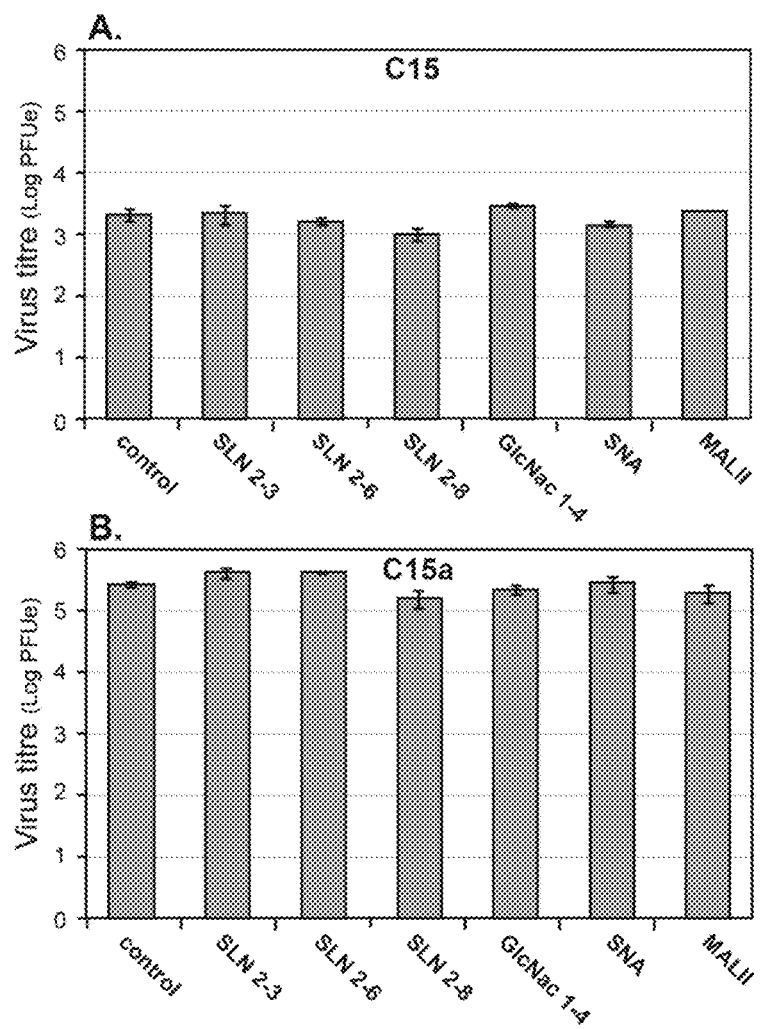

FIGS. 9A-9B—Glycan effects on virus binding assays. (A) Recombinant C15 or (B) polyclonal C15a were incubated in media with the indicated sialylated glycans (1 mg/ml, see below) before being tested for binding to HeLa-E8 cells. Virus ($5\times10^5$ PFUe) and glycan were mixed (30 min, 34° C.), then added to plated cells (30 min, room temp), before the samples were again incubated at 34° C. for an additional 30 min. The cells were washed (3×) before total RNA was extracted and assayed for C15 titer by RT-qPCR. For SNA and MALII samples, the cells, rather than virus were pretreated (100 μg/ml for 30 min, room temp) before the virus addition step. The plotted values are the averages of duplicate samples (n=2). Glycan reagents include: SLN 2-3 (3'-Sialy-N-acetyllactosamine, V-Labs, Inc), 1 mg/ml; SLN 2-6 (6'-Sialy-N-acetyllactosamine, V-Labs, Inc), 1 mg/ml; SLN 2-8 (Neu5Ac2-8Neu5Ac2-8Neu5Ac-sp-biotin, GlycoTech), 1 mg/ml; GlcNac 1-4 (GlcNAcb1-4GlcNAcb-sp-biotin, GlycoTech), 1 mg/ml; SNA (Sambucus Nigra Lectin, Vector Laboratories), 100 μg/ml; MAUI (Maackia Amurensis Lectin, Vector Laboratories), 100 μg/ml.

Figure 10:
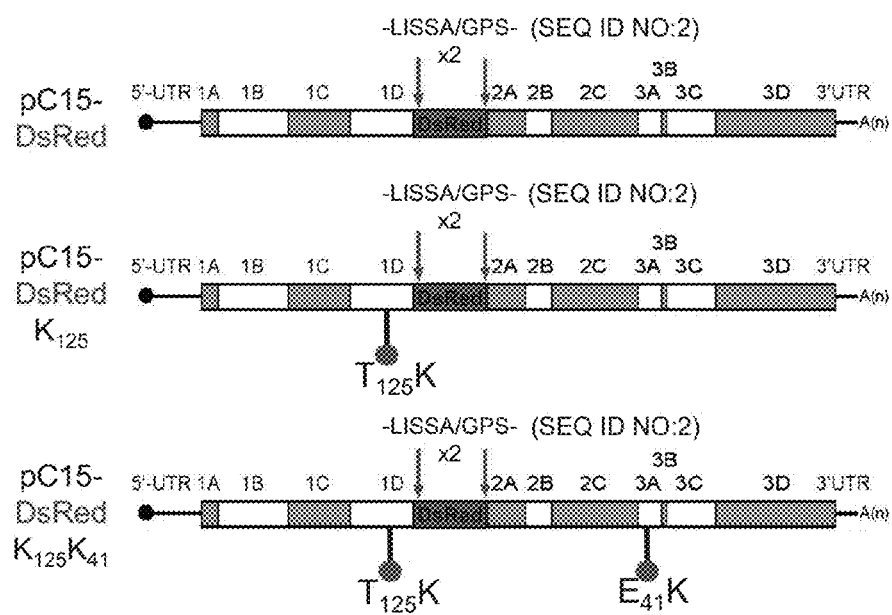

FIG. 10—C15-DsRed reporter cDNA clones. Schematic of the C15 genome shows localization of the DsRed-Express reporter gene flanked by 2A protease cleavage sites (-LISSA/GPS). C15-DsRed clone, a recombinant derivative of a clinical C15 isolate, and two C15-DsRed clones harboring one or both dominant adaptive mutations (VP1 $T_{125}K$, 3A $T_{41}K$) were engineered to produce recombinant viruses expressing DsRed-Express reporter protein upon viral RNA translation and replication.

Figure 11:
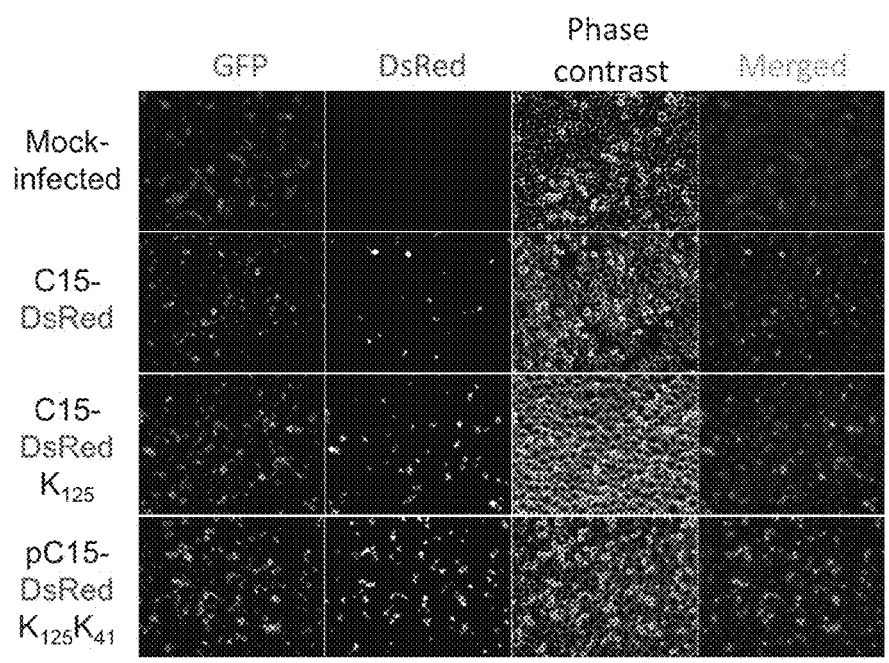

FIG. 11—RV-C15-DsRed replication in HeLa-E8 cells. Recombinant reporter C15 viruses with the indicated mutation(s) ($K_{125}$ in VP1, $K_{41}$ in 3A) were tested relative to reporter C15-DsRed in HeLa-E8 cells. Infected HeLa-E8 cells were visualized (48 h p.i.) for DsRed expression and photographed by fluorescent microscopy. Scale bar is 100 μm.

Figure 12:
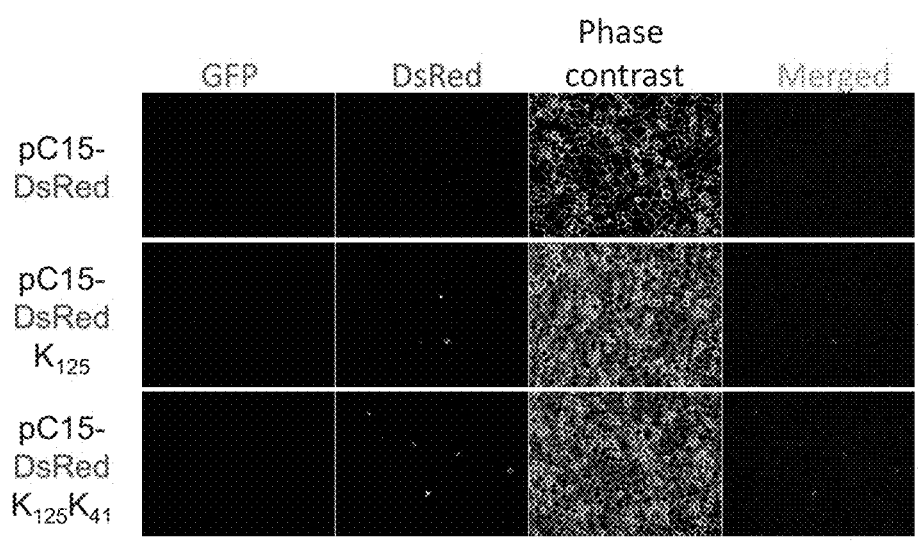

FIG. 12—RV-C15-DsRed replication in HeLa-H1 cells. Recombinant reporter C15 viruses with the indicated mutation(s) ($K_{125}$ in VP1, $K_{41}$ in 3A) were tested relative to reporter C15-DsRed in HeLa-H1 cells. Infected HeLa-H1 cells were visualized (48 h p.i.) for DsRed expression and photographed by fluorescent microscopy. Scale bar is 100 μm.

DESCRIPTION OF THE INVENTION

The present invention is a mutated rhinovirus C for enhanced virus yields after infection and induced visible cytopathic effect (CPE). In one embodiment, the mutated rhinovirus C may be a new reagent or tool for viral infectivity assays.

Applicants previously developed (by lentivirus transduction) a HeLa cell line (HeLa-E8) stably expressing the mutated CDHR3 sequence ($C_{529}Y$) with increased cell surface localization of the variant protein that supports propagation of rhinovirus C (RV-C) by infection. The RV-C propagation in the HeLa-E8 transduced cell line is the subject of pending U.S. patent application Ser. No. 14/836,327, incorporated herein in its entirety.

In one aspect, the present invention is a mutation of a RV-C clinical isolate for optimal propagation in a HeLa-H1 cell line or a transduced HeLa-E8 cell line expressing CDHR3. The rhinovirus C (RV-C) may be any known clinical isolate of RV-C. In one embodiment of the present invention, the mutated RV-C is a mutated version of clinical isolate C15. In another embodiment, the mutated RV-C is a mutated version of clinical isolate C2. In another embodiment, the mutated RV-C is a mutated version of clinical isolate C41.

Mutations of the present invention may be selected from $T_{125}K$ in protein VP1 in C15, a mutation structurally analogous to $T_{125}K$ in non-C15 strains, $E_{41}K$ in rhinovirus C15 protein 3A, and a mutation that is a positional equivalent of $E_{41}K$ in non-C15 strains. An isolated, mutated RV-C of the present invention may have a mutation $T_{125}K$ in rhinovirus C15 protein VP1, a structurally analogous mutation to T125K in a non-C15 strain, $E_{41}K$ in rhinovirus C protein 3A, or a positional equivalent mutation to E41K in a non-C15 strain. In one embodiment of the present invention the mutated RV-C has both mutations at T125, or its structurally analogous positions, and E41, or its positional equivalent residue. The mutation numbering is consistent with residue numbering found in the following publication: Y. A. Bochkov, A. C. Palmenberg, W. M. Lee, J. A. Rathe, S. P. Amineva, X. Sun, T. R. Pasic, N. N. Jarjour, S. B. Liggett, J. E. Gern, *Molecular modeling, organ culture and reverse genetics for a newly identified human rhinovirus C*, Nat. Med. 17(2011) 627-632.

The VP1 mutation numbering is different in strain C2 (wherein the mutation is at residue 122) and strain C41 (wherein the mutation is a at residue 124) whereas the 3A mutation numbering (wherein the mutation is at residue 41) is the same as in C15, as recorded in FIG. 6. As used herein "structurally analogous" refers to the mutation in non-C15 strains that is the equivalent to the VP1 protein $T_{125}K$ mutation in C15 and means that the mutation is at a structural position analogous to the position of $T_{125}K$ as defined in PDB file 5KOU, as illustrated and specifically pointed out in FIGS. 2A-2B. As used herein "a positional equivalent" refers to the 3A protein $E_{41}K$ mutation in non-C15 strains and means that the mutation is in a position in the sequence equivalent to the C15 E41 residue in 3A, as demonstrated in the WebLogo alignment illustrated in FIG. 2C.

For strain C15 amino acid residues are numbered from the amino-terminus of each individual viral protein, including position 125 in VP1 and position 41 in the 3A protein according to a system commonly used for picornaviruses. The GenBank accession number of the RV-C15 complete genome sequence is GU219984 and the corresponding polyprotein accession number is ACZ67658. Although the full-length polyprotein residues are consecutively numbered from 1 to 2153 in the GenBank entry, the mutated residues can still be easily found in the published sequence that has individual protein locations in the Features. The mutated residue positions in are $T_{692}K$ in VP1 and $E_{1454}K$ in 3A when using consecutive numbering from the amino-terminus of the whole polyprotein.

The rhinoviral genome consists of 3 coding regions designated P1, P2 and P3. The P1 region encodes the structural (or capsid) proteins whereas the P2 and P3 regions encode the nonstructural proteins associated with replication. There are four genes in P1 (1A, 1B, 1C and 1D) that encode four capsid proteins VP4, VP2, VP3 and VP1, respectively. Therefore, the VP1 protein is encoded by the 1D gene. As for the nonstructural proteins, gene and protein names are the same so the 3A protein is encoded by the 3A gene. FIG. 2A depicts the viral genome and contains the gene designations.

In one embodiment, the mutated RV-C strain of the present invention induces strong cytopathic effect and replicates vigorously in the HeLa-E8 cells, yielding more than a log higher level of infectious rhinovirus particles compared to that of parental clinical isolate. This adapted virus may be used for large-scale cost-effective production of RV-C by infection and for testing antiviral compounds by infectivity assays (such as virus plaque assay) or utilizing reporter-expressing adapted RV-C.

In some embodiments of the invention, the RV-C construct may additionally include a reporter. A reporter of the present invention may be any fluorescent protein cloned into a mutant or wild-type rhinovirus C. Reporters may include, but are not limited to DsRed and GFP. In one embodiment the reporter is DsRed. In another embodiment the reporter is GFP or enhanced GFP (eGFP).

In one embodiment the reporter is eGFP with the following amino acid sequence (SEQ ID NO:3):

```
VSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNS

HNVYIMADKQKNGIKVNFKIRHNIEDGSVQLADHYQQNTPIGDGPVLLP

DNHYLSTQSALSKDPNEKRDHMVLLEFVTAAGITLGMDELYK
```

In one embodiment the reporter is DsRed-Express with the following amino acid sequence (SEQ ID NO:4):

ASSEDVIKEFMRFKVRMEGSVNGHEFEIEGEGEGRPYEGTQTAKLKVTK
GGPLPFAWDILSPQFQYGSKVYVKHPADIPDYKKLSFPEGFKWERVMNF
EDGGVVTVTQDSSLQDGSFIYKVKFIGVNFPSDGPVMQKKTMGWEASTE
RLYPRDGVLKGEIHKALKLKDGGHYLVEFKSIYMAKKPVQLPGYYYVDS
KLDITSHNEDYTIVEQYERAEGRHHLF

The reporter may be cloned into the rhinovirus C construct using any linker sequence. The reporter may be cloned into any position in the rhinovirus construct such that the rhinovirus C may still infect and replicate similar to a construct without the reporter. In one embodiment the linker sequence is the authentic 2A protease ($2A^{pro}$) cleavage site (Leu-Ile-Ser-Ser-Ala-/Gly, SEQ ID NO:1) which attaches the reporter upstream of the viral open reading frame. In another embodiment, the linker sequence is a modified $2A^{pro}$ cleavage site with two additional amino acids (Leu-Ile-Ser-Ser-Ala-/Gly-Pro-Ser, SEQ ID NO:2), in which the reporter is introduced between VP1 and 2A.

In one version of the present invention, the adapted polyclonal C15a and recombinant C15-$T_{125}$K-$E_{41}$K derivative yields about 10-fold more virus progeny compared to the wild-type C15 isolate and induce strong cytopathic effect in HeLa-E8 cells. The mutated viruses in various embodiments described herein now enable large-scale cost-effective RV-C production by infection and the testing of RV-C infectivity by plaque assay. Since the 3A mutation and its positional equivalent could partially confer adaptation to other recombinant RV-C strains, the mutation can be engineered into additional cDNA clones to enhance virus yields and produce high-titer virus preparations.

These reagents will facilitate viral structure studies, CDHR3 investigations, and potentially, RV-C antiviral development. High titer RV-C preparations are essential for development of polyvalent RV vaccines. Reporter viruses with adaptive mutations can be readily used for monitoring virus spread at the single-cell level in vitro and for high-throughput testing of different antiviral compounds by fluorescent microscopy.

EXAMPLES

Example 1

The RV-C15 clinical isolate replicates well (more than 2-log increase in viral RNA from 2 h to 24 h post infection) in HeLa-E8 cells but induces very mild cytopathic effect (CPE) in this cell line. However, RV-C15 progeny yields after infection are still about 1-log lower compared to a HeLa-adapted isolate of RV-A16. The following exemplary embodiment demonstrates the development of a HeLa adapted RV-C15 variant to maximize replication levels and virus yields. The new progeny showed enhanced yields after infection and induced visible CPE, validating a new reagent for viral infectivity assays. Complete genome sequencing of the HeLa adapted RV-C15 variant (RV-C15a) identified mutations causing this more efficient replication. When introduced into RV-C15 cDNA, these mutations recapitulated the adaptive phenotypes, and moreover, could confer them to other RV-C isolates. The following exemplary embodiment also demonstrates incorporation of the beneficial mutations developed in RV-C15 into other RV-C isolates.

Materials and Methods

Cell Cultures

Bronchial epithelial tissue samples were obtained from residual surgical specimens and cultured at air-liquid interface (fully-differentiated) as described previously (Schroth et al., 1999; Ashraf et al., 2015). The protocol was approved by the University of Wisconsin-Madison Human Subjects Committee. H1-HeLa (ATCC# CRL-1958), HeLa-E8 (Bochkov et al., 2015) and WisL (human embryonic lung fibroblast) cells were grown in Eagle's Minimum Essential Medium (Lonza) supplemented by non-essential amino acids (Gibco) and 10% fetal bovine serum (Gemini).

Viruses and Infection

Recombinant rhinoviruses were produced by transfecting full-length T7 RNA transcripts synthesized in vitro from linearized plasmid cDNA, into WisL cells. Virus purification was by ultracentrifugation through a sucrose cushion as previously described (Bochkov et al., 2011; Nakagome et al., 2014). Cells grown in 12- or 24-well plates (monolayers) or in Transwell polycarbonate inserts (0.4 μm pore size, Corning; for differentiated cultures of PBE cells) were (typically) inoculated with virus at $2 \times 10^6$ PFUe per well (unless another dose is indicated) or ALT insert followed by incubation for 2-24 hours at 34° C. At harvest at 2 h p.i. (binding), the monolayers were washed (3×PBS) to remove any unattached inoculum, before lysis with RLT buffer (Qiagen), whereas at 24 h p.i. (replication) 100 μl of culture medium and whole cell lysate samples were collected to estimate total virus progeny yields. Virus titers (plaque-forming unit equivalents, PFUe) were determined by RT-qPCR according to standardized RNA preparations. Total RNA was extracted from harvested cells and media samples using RNeasy Mini kits (Qiagen). The RT-qPCR used Power SYBR Green PCR mix (Life Technologies) as previously described (Bochkov et al., 2011).

Inhibition of Virus Binding and Replication

Purified virus ($5 \times 10^5$ PFUe) was pre-incubated with tested compounds (sialic acid and sugar di- or trisaccharides, heparin or HS) for 30 min at 34° C. before inoculation of HeLa cell monolayers (30 min, room temp; 30 min, 34° C.). Cells were washed three times with PBS, lysed with the RLT buffer (Qiagen) and stored at −80° C. before total RNA extraction and RT-qPCR for C15. For SNA and MAUI samples, the cells, rather than virus were pretreated (100 μg/ml for 30 min, room temp) before the virus addition step. HeLa-E8 cells were washed with PBS containing 1 mM $MgCl_2$ and 1 mM $CaCl_2$ ($PBS^{++}$) and incubated for 2 hours at 37° C. with 2.5-10 U of heparinase I in $PBS^{++}$ before inoculation with purified virus ($10^6$ PFUe) for 1 hour at 34° C.

RNA Extraction and Quantitative (q) RT-PCR.

Total RNA was extracted using the RNeasy Mini kit (Qiagen). Viral RNA concentrations were determined by RT-qPCR using Power SYBR Green PCR mix (Life Technologies) as previously described (Bochkov et al., 2011).

PCR Amplification and Sequencing of Adapted RVs

In these studies, the parental C15 sequence was according to GenBank accession number GU219984. Total RNA from a sample of the polyclonal C15a (P10) grown in HeLa-E8 monolayers was extracted for RT reactions and primed with random hexamers (Life Technologies) or OligoT-r primer. The viral cDNAs were amplified using C15-specific primers (Table 1). A total of 14 genome-comprehensive PCR amplicons were sequenced directly as a population, and also cloned in pGEM-T Easy vectors, where out-growth colonies were sequenced individually (n=10 clones per each product). Sequence data were assembled and compared using Lasergene™ v. 12 software (DNAStar). Polyclonal HeLa-adapted A16 (P10) was treated similarly, except that population and cDNA clone sequencing focused on only two genome regions: the VP3-VP1 genes (PCR1), and the 2C-3C genes (PCR2) (Table 1).

TABLE 1

Primers used for PCR, cloning, and sequencing

| Primer | Sequence (5'-3') | Assay |
|---|---|---|
| C15-5'end-f | TTAAAACTGGGTATAGGTTGTTCC (SEQ ID NO: 5) | C15a PCR |
| NheI-r | TGGATGGGTCCTGAGAAAAGTC (SEQ ID NO: 6) | and |
| NheI-f | ACTTTGCCCTGGGTGTGTATGAT (SEQ ID NO: 7) | sequencing |
| C15-PasI-r | ACTTTGCCCTGGGTGTGTATGAT (SEQ ID NO: 8) | |
| BamHI2-r | TCATTTCTAGGGGCAGAACAAG (SEQ ID NO: 9) | |
| C15-VP2-f | TGGTGCACTCATAGTCGCGGT (SEQ ID NO: 10) | |
| MluI-f | AACGCCAAGGCTTGCCAACG (SEQ ID NO: 11) | |
| C15-VP1-r | CTATTGTGGATTCTGGGGTTGCGT (SEQ ID NO: 12) | |
| BlpI-r | GACTCCCGGGGCCTGGAACATTGGTACTA (SEQ ID NO: 13) | |
| C15-VP1-f | ATATTGGGTGCCATGGAGATTGGT (SEQ ID NO: 14) | |
| BlpI-f | GATTGTCGACCTAACTCTAGTGGACCTGATG (SEQ ID NO: 15) | |
| PflMI-r | TGGGTGAGTCCTCTAGCGATT (SEQ ID NO: 16) | |
| PflMI-f | GTTATCTAGACCATAGGCATGAACCAGTTTG (SEQ ID NO: 17) | |
| MfeI-r | CGTTGGTGTTCTGGGATGAACCT (SEQ ID NO: 18) | |
| MfeI2-r | CCGTCAATTGTGACAGAGTCACCA (SEQ ID NO: 19) | |
| C15-2C-f | AGTAGAGCAGCTGAGGCATGAGAAT (SEQ ID NO: 20) | |
| MfeI-f | GAATTCTAGATAACTGTGCGGTGGTGC (SEQ ID NO: 21) | |
| C15-3D-r | GAAGTTTGGTTACATCCTTTGTCAC (SEQ ID NO: 22) | |
| BamHI-r | TGTACTGCCCTTGTCTGGTGGAG (SEQ ID NO: 23) | |
| NdeI-f | ATTATAGCATATGGTGATGATGTAGT (SEQ ID NO: 24) | |
| 3UTR-r | ATATCCCGGGTTCGAATCGA (SEQ ID NO: 25) | |
| OligoT-r | ATATCCCGGGTTCGAATCGA(T) (SEQ ID NO: 26) | |
| | | |
| VP1-K125-f | GTAACCAACAACAaAGGGTTGATGCAAATAATG (SEQ ID NO: 27) | C15-K125/ |
| VP1-K125-r | CATTATTTGCATCAACCCTtTGTTGTTGGTTAC (SEQ ID NO: 28) | K41 |
| 3A-K41-f | ACTCAACCATAaAGAGGGATTTTAATTATGTGC (SEQ ID NO: 29) | cloning |
| 3A-K41-r | AATCCCTCTtTATGGTTGAGTTTGCTTTAC (SEQ ID NO: 30) | |
| | | |
| C2-NheI | ACATCAGCTAGCATACATTGGCGCT (SEQ ID NO: 31) | C2-K122/ |
| C2-EcoNI-f | TTACACCCCTCCAGGAGGTGGAT (SEQ ID NO: 32) | K41 |
| C2-EcoNI-r | ACTCTGATACTGCCTGACCAGTTG (SEQ ID NO: 33) | cloning |
| C2-K122-f | GTAACTAATAACAAAGGTTTAATGCAAATCATGTATG (SEQ ID NO: 34) | |
| C2-K122-r | GCATTAAACCTTTGTTATTAGTTACTATAGTTACTTCC (SEQ ID NO: 35) | |
| C2-BlpI-r | ACATAATATGCTGAGCCTAAACCAGTAAAG (SEQ ID NO: 36) | |
| C2-K41-f | CTTATCCTGAGGAGCTCCACCACCTTAAAGAGACACAT AGACAGAGTACAGCAGGC (SEQ ID NO: 37) | |
| C2-SexAI-f | GCAGATGTAGGGACAGCAACAC (SEQ ID NO: 38) | |
| C2-SexAI-r | ATTTCCAAGTACACCACCACACTGA (SEQ ID NO: 39) | |
| C2-BsiWI | AAGTAACGTACGGTAAATCAATACCATAC (SEQ ID NO: 40) | |
| | | |
| C41-K124 gBlock | TGGTACCAAACTGATTTCATCCCTTCAGTTAACGCAGGC ACAGGTACCATCATTGCTACTTGTAGCGCCTGCCCTGAC ATGTCTGTTAGGATGATGAGGGATAGTCCAATGATGAA GCAAGAAGGGAAGCTCCAAAACAATGATCCCGTGGAAT CCTTCATTCACACAACGCTAGAGGAAGTACTAGTTGTG CCAGACACCAAACCATCAGGCCCACAACATACTACCAA ACCATCAGCACTTGGGGCGATGGAAATTGGAGCATCAA GCGATGCAACTCCTGAATCAGTGATAGAAACTAGGTAT GTGTTCAACACAAACACCAATGCAGAAGCTGACATTGA AATGTTTCTGGGTAGATCAGCTTTATGGGCTAATTTGAC ACTTAGAGAAGGATTCACTGAATGGGAGATAAATTTCC AGGAGAATGCACACATCAGGAAGAAGTTTGAACTATTC ACCTATATTAGGTTTGACATGGAAGTTACAATAGTAAC GAACAACAaAGGGTTAATGCAGATCATGTTCGTGCCAC CTGGAATCACTGGTCCAAAGAATGCTGAGGATATTCGA TGGGATTCCGCCTCA (SEQ ID NO: 41) | C41-K124 cloning |
| | | |
| C41-NheI | ATCCTTGCTAGCACAAATTTGGACA (SEQ ID NO: 42) | C41-K41 |
| C41-K41-f | TGGTTCTACAGTAAAAAGGGATTTCAACTATGTTCATTAC (SEQ ID NO: 43) | cloning |
| C41-K41-r | TGAAATCCCTTTTTTACTGTAGAACCAGCCCTTCCA (SEQ ID NO: 44) | |
| C41-ApaI | ATGTTCTGGGCCCTGTAGAGTAGCT (SEQ ID NO: 45) | |
| C41-AjuI | AGAAGCAATGCTTGGTGTGCAT (SEQ ID NO: 46) | |
| | | |
| RV16-NcoI | TCTACAATCCACAGTGTCATTGGT (SEQ ID NO: 47) | RV-A16a1 |
| RV16-BstXI | ACAATACGCGAGCACAAAGTTC (SEQ ID NO: 48) | PCR and |
| RV16-EcoRV | GATAATCAGAGTGTAGTAATAATGGATG (SEQ ID NO: 49) | cloning |
| RV16-SnaBI | AGTCATCTTCTGATTCAGGTATGTACT (SEQ ID NO: 50) | |
| RV16-2C-seq | TTAGAAATTCTTCAGATCCGCA (SEQ ID NO: 51) | |

Construction of RV Infectious Clones with Adaptive Mutations

Full-length cDNA materials encoding C15, C2, C41 and A16 (pR16.11) infectious genomes have been described (Lee & Wang, 2003; Bochkov et al., 2011; Nakagome et al., 2014). pR16.939 encodes an RV-A16 clinical isolate that was cloned and provided by Dr. Wai-Ming Lee (Biological Mimetic Inc, Frederick, Md.). Mutated derivatives were engineered by two-step PCR using appropriate flanking and internal primers or dsDNA gBlock gene fragments (Table 1) synthesized by Integrated DNA Technologies (Coralville, Iowa). All plasmid DNAs were verified in the regions of interest by sequencing, and then purified by Plasmid Maxi kits (Qiagen) before use in RNA synthesis reactions with T7 polymerase (Promega).

Plaque Assay

The procedure was done as described previously (Sherry & Rueckert, 1985; Wang et al., 1998) with some modifications. HeLa-E8 cells monolayers were prepared by plating $2.5 \times 10^6$ cells per 60-mm dish and then incubation at 37° C. overnight. Cells were infected with 10-fold serial dilutions of C15a virus for 30 min (15 min, room temp, 15 min 34° C.). The infected monolayers were overlaid, first with 2.5 ml of 0.8% agarose (Seakem ME) in medium P6 (Sherry & Rueckert, 1985), and then (after the agarose solidified) with 2.5 ml of medium P6 containing 4 mM L-glutamine, 4 mM oxaloacetate, 2 mM pyruvate, and 11.2 mM D-glucose. Plaques were allowed to develop at 34° C. for 96 h and then visualized by crystal violet staining.

Results

Serial Passaging of RV-C15 in HeLa-E8 Cells Improves Viral Growth

Preparations of the original recombinant RV-C15 virus (C15) grow well in HeLa-E8 cells; however, the progeny yields are about a log lower compared to a HeLa-adapted (a) strain of RV-A16 (A16a) (FIG. 1A) To adapt the C15 virus, HeLa-E8 cells, grown in 12-well plates, were infected with a sample of recombinant C15 at an MOI of 10 plaque-forming unit equivalents (PFUe). The virus inoculum was replaced with fresh growth medium 2 h post-infection (p.i) after which the cells were incubated for 72 h at 34° C., then harvested. A sample of the clarified cell lysate was used for the next round of infection in fresh HeLa-E8 cells, after titering for PFUe, and the blind-passage serial process (MOI of 10) was repeated a total of 10 times (P1 to P10). At each step, the virus titer was monitored by RT-qPCR, and by P10, this value had increased by more than 10-fold, relative to the P1 starting sample (FIG. 1B). After only five of these passages, however, visual cell monitoring clearly showed strong cytopathic effects (CPE), such as detached and rounded cells. In the P10 infected cells, almost complete cell lysis was evident at 72 h p.i. (FIG. 1C).

This adaptation ultimately resulted in virus samples (C15a) with increased (≥10-fold) binding to HeLa-E8 cells, and progeny yields that were consistently at least 10× higher than the initial C15 material. (FIG. 1A). Surprisingly, when C15a was tested for binding to non-transduced HeLa-H1 cells (parental line to HeLa-E8), the adaptation had clearly affected this parameter too, and the virus reacted nearly equivalently with both cell lines. However, C15a replication in HeLa-E8 was consistently more than 1.5 log higher when compared to the parental HeLa-H1 cells. Similarly, C15a infections caused lysis of HeLa-E8, but this virus could not lyse infected parental cells. When evaluated for infective potential to fully-differentiated cultures of human primary bronchial epithelial cells grown at air-liquid interface, the C15a sample was found to maintain similar cell-binding potential relative to C15, but the replication potential now tended to be about a log lower for progeny titer (FIG. 1A).

Identification of Mutations in C15a Genome Responsible for Adapted Phenotype

To determine the genetic basis of the adapted viral phenotype, total RNA was isolated from the polyclonal P10 virus lysate and 14 overlapping cDNA fragments were amplified by RT-PCR. Complete genome sequencing revealed several missense mutations in both the structural (VP3 and VP1) and nonstructural (3A) proteins of RV-C15a compared to parental RV-C15-wt whereas no changes were found in UTRs (FIG. 2A). Sequence and structural analyses of the highly variable VP1 protein revealed that threonine in position 125 is found in 54% of RV-C types and mapped this mutation to the viral surface surrounding a "hole" at the 5-fold axis of symmetry (FIG. 2B) whereas glutamic acid residue in position 41 of 3A, located at the junction between the helical hairpin and hydrophobic domain at the C-terminal end of the protein, is highly conserved in all sequenced RV-C types as well as in RV-A and RV—B types (FIG. 2C). The only other amino acid residue found at this position in 16 out of 335 sequenced RV strains is also negatively charged aspartic acid. Three dominant (i.e. found both by direct sequencing of PCR products and in the majority of sequenced clones) missense mutations were introduced individually or in combination into the RV-C15 cDNA, and the corresponding recombinant viruses were tested for infectivity.

The results demonstrate that adaptation is acquired by only two key mutations responsible for increased binding ($T_{125}K$ in VP1) and replication ($E_{41}K$ in 3A) in HeLa-E8, respectively (FIG. 3A). The third amino acid change ($P_{215}S$) found in VP3 did not have any additive effect on virus binding when introduced together with $T_{125}K$ in VP1 (data not shown). Recombinant RV-C15 containing both of these mutations showed binding and replication levels similar to polyclonal RV-C15a in both control and transduced HeLa cells. Interestingly, a single $E_{41}K$ mutation in 3A not only enhanced RV-C15 replication in HeLa-E8 but showed about 7-fold increase in vRNA levels in control HeLa-H1 cells confirming that low-level viral entry (and RNA replication) can occur even in the absence of $T_{125}K$ mutation in VP1. Infection with RV-C15-$K_{125}$ induced mild but visible CPE in HeLa-E8 48-72 h p.i., whereas RV-C15 possessing both mutations ($K_{125}$ and $K_{41}$) induced stronger CPE which was comparable to that observed after RV-C15a infection (FIG. 3B).

Heparan Sulfate Inhibits C15a Binding

Figures 4A, 4B, 4C, 4D, 4E:
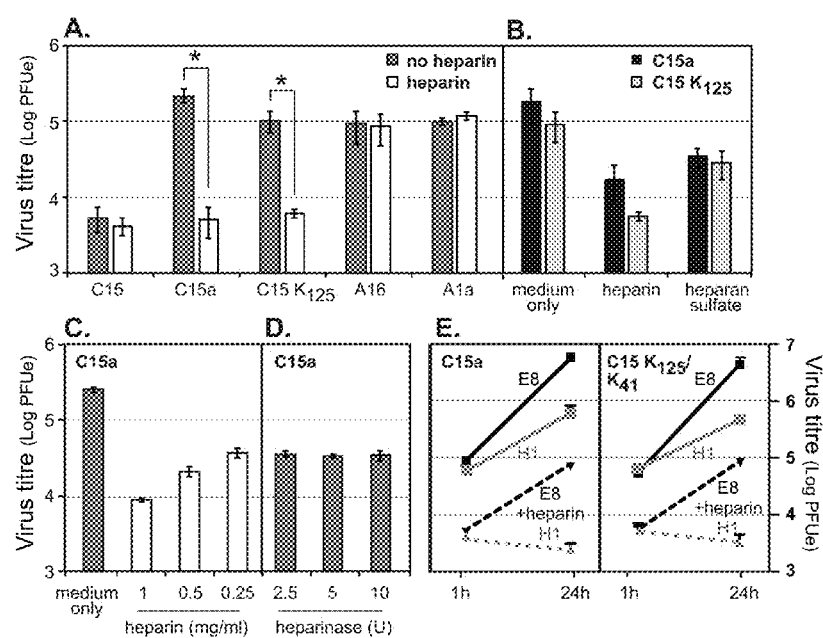

Some RV types and other related enteroviruses can utilize cell surface heparan sulfate (HS) or sialic acid glycans as functional receptors (Zautner et al., 2003; Vlasak et al., 2005; Khan et al., 2007; Israelsson et al., 2010; Tan et al., 2013; Nakagome et al., 2014; Liu et al., 2015). To investigate the novel receptor specificity of RV-C15a vs. wild-type, virus binding was screened in the mammalian glycan array containing 609 targets (Consortium for Functional Glycomics). RV-C15a and RV-C15-$K_{125}$ exhibited low-level binding to some sialylated glycans and disaccharides whereas RV-C15-wt did not (FIG. 8). However, preincubation with these and some additional glycans did not inhibit RV-C15a binding (FIG. 9). In parallel experiments, however, the recombinant and adapted C15a mutant panels were also tested for heparin (as a less expensive substitute for HS) and HS inhibition effects. A16 and Ala viruses, which use respectively ICAM-1 and LDLR receptors, were not affected by heparin in their interactions with HeLa-E8 cells (FIG. 4A). The same was true for the unadapted C15 virus which recognizes cells through CDHR3-mediated reactions (Bochkov et al., 2015). But the adaptive mutations within both C15a and C15 $K_{125}$, now made both viruses susceptible to heparin, reducing their binding titers 17 and 44-fold, respectively, or back down to the values without the adaptive mutation. Heparin and HS (1-2 mg/ml) both had this effect (FIG. 4B), and the observed degree of inhibition was dependent upon the dose of administered glycan (FIG. 4C). In agreement with other described properties of sulfated proteoglycans, enzymatic pretreatment of HeLa-E8 cells with heparinase I reduced C15a binding more than 7-fold, because presumably, the adapted virus now had fewer cellular-displayed HS binding sites available to it (FIG. 4D). Interestingly, when the adapted viruses (polyclonal population or recombinant) were tested comparatively, pretreatment with heparin abolished both binding and replication in the HeLa-H1 cells, but nonetheless, both viruses still replicated (to a degree) in HeLa-E8 cells despite the heparin treatment (FIG. 4E).

Development of an Infectivity Assay for RV-C

Until now, it has not been possible to assess RV-C infectivity so investigators used quantitative RT-PCR to measure viral RNA concentration (Bochkov et al., 2011; McLeish et al., 2012; Schibler et al., 2012; Brebion et al., 2015). To develop a plaque assay for RV-C, we infected HeLa-E8 monolayers with serially tenfold diluted RV-C15a under agarose overlay using standard plaque assay protocol and confirmed formation of small to medium size plaques 96 h p.i. (FIG. 5). This assay enables direct testing of viral titer (i.e. the number of infectious virus particles in plaque forming units), and purification of clonal populations of RV-C. The ratio of total viral particles (or viral RNA copies) to infectious particles in RV-C15a suspensions purified by sucrose-cushion centrifugation was about 200, which is quite similar to other laboratory strains of RV (e.g. RV-A16).

Effects of VP1-$K_{125}$ and 3A-$K_{41}$ Mutations on Binding and Replication of RV-C2 and C41

To test whether two amino acid changes found in RV-C15a are type-specific, similar mutations were made in RV-C2 and RV-C41 cDNAs and recombinant viruses were prepared and tested for infectivity in HeLa cells. Mutations in VP1 ($K_{122}$ in RV-C2 and $K_{124}$ in RV-C41) corresponding to $K_{125}$ found in RV-C15a had no effect on virus binding properties indicating that effects of capsid amino acid changes are type-specific (FIG. 6A-6B). However, $K_{41}$ mutation in 3A also improved viral replication (2-7 fold) of the both RV-C types. Similarly to RV-C15, the $E_{41} \rightarrow K$ mutation not only enhanced viral replication in HeLa-E8 but also showed increase (3-8 fold) in vRNA levels in control HeLa cells indicating broader species-wide effects of this highly conserved amino acid on 3A protein properties.

RV-A16 Adaptation to HeLa Cells is Mediated by Mutations in 2C

We next used the same serial passaging approach to determine whether adaptation of a RV-A16 clinical isolate for growth in HeLa cells would occur via similar molecular mechanisms. As with the RV-C15 adaptation kinetics, strong visible CPE was noticed after only five serial passages, and almost complete cell lysis was observed at P10 (FIG. 7A). The RV-A16 adaptation also resulted in about one log higher virus progeny yields compared to wt virus (FIG. 7C). Partial sequencing of the PCR fragment comprising partial 2C, complete 3A and 3B and partial 3C genes revealed a total of four amino acid changes in C-terminal part of 2C ($Q_{261} \rightarrow R$, $D_{264} \rightarrow Y$, $K_{268} \rightarrow R$, $K_{281} \rightarrow R$) that were found in close proximity to each other either singly or in combinations in the same clone (FIG. 7B). Interestingly, three out of four mutations are substitutions of uncharged glutamine or positively charged lysine with arginine (which also carries a positive charge), and one mutation replaces negatively charged aspartic acid with a tyrosine residue. Infectivity tests with the recombinant RV-A16 viruses (n=4) carrying these mutations showed that each of them enhanced viral replication to the levels of adapted RV-A16. Of those three arginine mutations, the $Q_{261} \rightarrow R$ seems to be essential for adaptation because it is dominant among sequenced clones, found alone or in combination in all three tested clones with the HeLa-adapted phenotype, and also present in another adapted RV-A16 strain (pR16.11) described previously (Lee & Wang, 2003). These findings demonstrate that adaptive mutations in RV non-structural genes are heterogeneous and species and/or type specific, but boost viral replication efficiency to a similar degree (about one log increase in progeny yields vs wt).

Discussion

RV strains that are adapted to cell lines have proven to be very useful for producing high-titer viral suspensions, infectivity assays, and in investigations of molecular pathogenesis. To produce the first laboratory adapted RV-C, serial passages were performed in a transduced HeLa-E8 cell line, and achieved replication levels and visible CPE similar to those of other RV adapted strains. Infectivity tests identified two key mutations responsible for increased binding ($T_{125}K$ in VP1) and replication ($E_{41}K$ in 3A) in HeLa-E8, respectively. Surprisingly, RV-C15a acquired an ability to bind to and even replicate in parental H1-HeLa cells, however, replication was much lower compared to that in HeLa-E8 cells, most probably due to inefficient cell entry in the absence of CDHR3 expression. Competitive inhibition experiments to identify the novel binding specificity of RV-C15a showed that HS ubiquitously expressed on cell surfaces might serve as an attachment factor in HeLa cells.

Receptor specificity switch has been documented for some major receptor group RVs (e.g. RV-A89) that were adapted for growth in ICAM-1-deficient cells by serial or alternate passages in HEp-2 and HeLa cells (Reischl et al., 2001; Vlasak et al., 2005). A HEp-2-adapted RV-A89 variant can utilize HS proteoglycans as a cellular receptor (Vlasak et al., 2005). Moreover, it was demonstrated that even a wild-type RV-A54 isolate could use HS proteoglycan as an alternate receptor without adaptation; however, infection via HS is less efficient than that via ICAM-1 (Khan et al., 2007). In contrast to RV-A89, RV-C15 adaptation by passaging in HeLa cells occurred in the absence of selective pressure for binding specificity change. This process has also been observed in some other picornaviruses and alphaviruses (Sa-Carvalho et al., 1997; Klimstra et al., 1998; Smit et al., 2002). Heparin, HS, and heparinase I treatment all inhibited RV-C15a and RV-C15-$K_{125}$ binding to HeLa-E8 cells to the levels of RV-C15-wt, suggesting that viral binding to CDHR3 was still preserved. In agreement with proposed interactions with negatively charged HS, recently resolved cryo-EM structure of RV-C15a maps the mutated $K_{125}$ residue in VP1 to the viral surface surrounding a "hole" at the 5-fold axis of symmetry and rendering the surface more basic (Liu et al., 2016). Interestingly, when similar mutation in VP1 was engineered in RV-C2 and RV-C41 cDNAs, virus binding properties were not affected indicating type-specificity of $T_{125} \rightarrow K$ effects on viral binding.

Picornaviruses replicate their RNA on reorganized cellular membrane structures designated "replication organelles" with the lipid composition significantly different from cellular membranes (Belov, 2014; van der Linden et al., 2015). It has been shown that enteroviral non-structural proteins 2BC and 3A possessing hydrophobic domains are involved in this process by interacting with a number of host cell proteins including Golgi-specific brefeldin A resistance guanine nucleotide exchange factor 1 (GBF1), phosphatidylinositol 4-kinase type III β (PI4KIIIβ) and the Golgi adaptor protein acyl-CoA-binding domain-containing protein 3 (ACBD3) (Wessels et al., 2006; van der Linden et al., 2015). Although less information is available on RV specifically, Mousnier et al. have demonstrated that transient expression of RV-A16 3A protein by transfection disrupts the Golgi structure and inhibits cellular protein secretion (Mousnier et al., 2014). RV replication depends on GBF1 and PI4KIIIβ but not on ACBD3, and PI4KIIIβ recruitment to replication sites is mediated by the 3A protein (Dorobantu et al., 2015). Interestingly, single-point mutations in 3A protein of RV and some other related picornaviruses allowed them to aquire resistance to some antiviral compounds (e.g. enviroxime) via bypassing their replication dependency on host factors such as PI4KIII (Heinz & Vance, 1995; van der Schaar et al., 2012; Dorobantu et al., 2016).

Notably, single mutation of highly conserved $E_{41}$ to K in RV-C15 3A protein enhanced viral replication in HeLa-E8, and to a lesser extent in CDHR3-deficient H1-HeLa cells indicating an alternative low-level viral entry mechanism likely independent of both CDHR3 and HS binding. Moreover, the amino acid change in 3A also enhanced replication of the additional RV-C types, suggesting that this mutation could enhance replication of RV-C species in general, perhaps by optimizing 3A for replication complex formation in HeLa cells.

In summary, this exemplary embodiment demonstrates developed the first lab strain of RV-C adapted for efficient growth and induction of strong CPE in transduced HeLa-E8 cells, and identified mechanisms for adaptation related to increased binding via interaction with HS proteoglycans ($T_{125} \rightarrow K$ in VP1) and enhanced replication ($E_{41} \rightarrow K$ in 3A), respectively.

Example 2

The following exemplary embodiment describes reporter viruses useful in high-throughput screens for compounds with antiviral activity against rhinovirus C and in tracking viral spread and antiviral responses at a single cell level.

The eGFP gene was cloned into the RV-C15 infectious clone (pC15-Rz-GFP) with the authentic 2A protease ($2A^{pro}$) cleavage site (Leu-Ile-Ser-Ser-Ala-/Gly, SEQ ID NO:1) as a linker preceding the viral open reading frame (ORF). Virus replication in transfected cells was confirmed by the development of specific cytopathic effects (cell rounding and detachment) and eGFP signal accumulation (from 8 to 24 h post transfection) determined by fluorescent microscopy, however, the progeny virus was not infectious to differentiated primary bronchial epithelial (PBE) cells.

A second version of the reporter cDNA (pC15-Rz-GFPv.2) was constructed by cloning in the eGFP sequence between VP1 and 2A using $2A^{pro}$ cleavage site extended by two amino acids (Leu-Ile-Ser-Ser-Ala-/Gly-Pro-Ser, SEQ ID NO:2). The resulting reporter virus replicated well in PBE cells which allowed for the monitoring of virus spread and replication by fluorescent microscopy. Similar constructs containing the DsRed reporter also produced infectious virus progeny in PBE cells. The results demonstrate utility of both loci of reporter sequences in viral genome and cleavage site lengths.

FIG. 10 shows the constructs of C15-DsRed reporter clones, including a recombinant derivative of a clinical C15 isolate (C15-DsRed), and two C15-DsRed clones harboring one or both dominant adaptive mutations (VP1 $T_{125}K$, 3A $T_{41}K$) engineered to produce recombinant viruses expressing DsRed-Express reporter protein upon viral RNA translation and replication.

Referring to FIGS. 11-12, fluorescent microscopy confirmed increased replication and visible CPE of C15-DsRed-$K_{125}K_{41}$ compared to C15-DsRed reporter virus. HeLa-E8 cells (FIG. 11) are transduced cells stably expressing CDHR3-$Y_{529}$ variant protein whereas control HeLa cells (FIG. 12) are the parental cell line H1-HeLa (ATCC CRL1958).

We claim:

1. An isolated mutated rhinovirus C, wherein the mutation is $E_{41}K$ in rhinovirus C protein 3A or a mutation in the amino acid at a positional equivalent of $E_{41}$ in protein 3A to K in non-C15 strains.

2. The virus of claim 1, wherein the rhinovirus C is a clinical isolate selected from the group consisting of C15, C41, and C2.

3. The virus of claim 2, wherein the rhinovirus C is clinical isolate C15 and the mutation comprises $E_{41}K$ in rhinovirus C protein 3A.

4. The virus of claim 2, wherein the rhinovirus C is clinical isolate C15 and the mutation comprises both $E_{41}K$ in rhinovirus C protein 3A and $T_{125}K$ in rhinovirus C protein VP1.

5. The virus of claim 2, wherein the rhinovirus C is clinical isolate C41 and the mutation is $E_{41}K$ in rhinovirus C protein 3A in strain C41.

6. The virus of claim 2, wherein the rhinovirus C is clinical isolate C2 and the mutation is $E_{41}K$ in rhinovirus C protein 3A in strain C2.

7. The virus of claim 1, wherein the mutated rhinovirus C additionally comprises a reporter.

8. The virus of claim 7, wherein the reporter is selected from the group consisting of DsRed and GFP.

9. The virus of claim 7, wherein the reporter is positioned upstream of a viral open reading frame and linked by SEQ ID NO:1.

10. The virus of claim 7, wherein the reporter is between VP1 and 2A and linked by SEQ ID NO:2.

11. A method of propagating rhinovirus C, comprising the step of infecting a transduced cell line expressing CDHR3 with the mutated rhinovirus C of claim 1.

12. The method of claim 11, wherein the cell line is a HeLa-E8 cell line.

13. The method of claim 11, wherein the rhinovirus C is a clinical isolate selected from the group consisting of C15, C41, and C2.

14. The method of claim 13, wherein the rhinovirus C is clinical isolate C15 and the mutation comprises both $T_{125}K$ in rhinovirus C protein VP1 and $E_{41}K$ in rhinovirus C protein 3A.

15. A method of creating a mutated rhinovirus C, wherein the method comprises the steps of introducing $E_{41}K$ in rhinovirus C protein 3A of strain C15 or a mutation that is a positional equivalent of $E_{41}K$ in non-C15 strains, and isolating the mutated rhinovirus C.

16. An isolated mutated rhinovirus C produced by the method of claim 15.

* * * * *

UNITED STATES PATENT AND TRADEMARK OFFICE
CERTIFICATE OF CORRECTION

Page 1 of 1

PATENT NO. : 10,253,300 B2
APPLICATION NO. : 15/232913
DATED : April 9, 2019
INVENTOR(S) : Yury A. Bochkov et al.

It is certified that error appears in the above-identified patent and that said Letters Patent is hereby corrected as shown below:

In the Specification

Column 1, Line 36, "Gem" should read --Gern--.

Column 4, Line 32, "5p8" should read --Sp8--.

Column 4, Line 34, "5p17" should read --Sp17--.

Column 4, Line 57, "MAUI" should read --MAL II--.

Column 8, Line 46, "MAUI" should read --MAL II--.

Signed and Sealed this
Eighteenth Day of June, 2019

Andrei Iancu
*Director of the United States Patent and Trademark Office*